US009610581B2

(12) United States Patent
Handique et al.

(10) Patent No.: US 9,610,581 B2
(45) Date of Patent: Apr. 4, 2017

(54) SYSTEM AND METHOD FOR CAPTURING AND ANALYZING CELLS

(71) Applicant: DeNovo Sciences, Inc., Plymouth, MI (US)

(72) Inventors: Kalyan Handique, Plymouth, MI (US); Kyle Gleason, Plymouth, MI (US); Austin Payne, Plymouth, MI (US); Priyadarshini Gogoi, Plymouth, MI (US); Saedeh Sepehri Javdani, Plymouth, MI (US); Christopher Siemer, Plymouth, MI (US); Yi Zhou, Plymouth, MI (US)

(73) Assignee: DeNovo Sciences, Inc., Plymouth, MI (US)

( * ) Notice: Subject to any disclaimer, the term of this patent is extended or adjusted under 35 U.S.C. 154(b) by 0 days.

(21) Appl. No.: 14/863,191

(22) Filed: Sep. 23, 2015

(65) Prior Publication Data

US 2016/0008814 A1    Jan. 14, 2016

Related U.S. Application Data

(63) Continuation of application No. 14/208,298, filed on Mar. 13, 2014, now Pat. No. 9,174,216.

(60) Provisional application No. 61/894,150, filed on Oct. 22, 2013, provisional application No. 61/829,528, filed on May 31, 2013, provisional application No. 61/779,049, filed on Mar. 13, 2013.

(51) Int. Cl.
| | |
|---|---|
| *G01N 31/00* | (2006.01) |
| *G01N 33/53* | (2006.01) |
| *B01L 3/00* | (2006.01) |
| *B01L 7/00* | (2006.01) |
| *G01N 35/00* | (2006.01) |
| *G01N 35/10* | (2006.01) |
| *C12Q 1/68* | (2006.01) |
| *G01N 33/569* | (2006.01) |

(52) U.S. Cl.
CPC ... *B01L 3/502761* (2013.01); *B01L 3/502715* (2013.01); *B01L 3/527* (2013.01); *B01L 7/00* (2013.01); *C12Q 1/686* (2013.01); *C12Q 1/6841* (2013.01); *G01N 33/56972* (2013.01); *G01N 35/0098* (2013.01); *G01N 35/1079* (2013.01); *B01L 3/5635* (2013.01); *B01L 2200/027* (2013.01); *B01L 2200/0652* (2013.01); *B01L 2300/0816* (2013.01); *B01L 2300/0832* (2013.01); *B01L 2300/0864* (2013.01); *B01L 2300/185* (2013.01); *B01L 2400/0487* (2013.01); *B01L 2400/0683* (2013.01); *G01N 2333/46* (2013.01)

(58) Field of Classification Search
None
See application file for complete search history.

(56) References Cited

U.S. PATENT DOCUMENTS

| | | | |
|---|---|---|---|
| 644,134 | A | 2/1900 | Gastineau |
| 4,551,435 | A | 11/1985 | Liberti et al. |
| 4,710,635 | A | 12/1987 | Chupp |
| 5,266,269 | A | 11/1993 | Niiyama et al. |
| 5,491,343 | A | 2/1996 | Brooker |
| 5,851,488 | A | 12/1998 | Saul et al. |
| 5,883,370 | A | 3/1999 | Walker et al. |
| 5,888,370 | A | 3/1999 | Becker et al. |
| 5,993,630 | A | 11/1999 | Becker et al. |
| 5,993,632 | A | 11/1999 | Becker et al. |
| 6,016,712 | A | 1/2000 | Warden et al. |
| 6,127,177 | A | 10/2000 | Toner et al. |
| 6,133,030 | A | 10/2000 | Bhatia et al. |
| 6,150,180 | A | 11/2000 | Parce et al. |
| 6,174,683 | B1 | 1/2001 | Hahn |
| 6,221,663 | B1 | 4/2001 | Bhatia et al. |
| 6,228,624 | B1 | 5/2001 | Terstappen |
| 6,287,832 | B1 | 9/2001 | Becker et al. |
| 6,365,362 | B1 | 4/2002 | Terstappen et al. |
| 6,410,724 | B1 | 6/2002 | Dejean et al. |
| 6,433,134 | B1 | 8/2002 | Patron et al. |
| 6,525,997 | B1 | 2/2003 | Narayanaswami et al. |
| 6,563,634 | B2 | 5/2003 | Shimada et al. |
| 6,623,983 | B1 | 9/2003 | Terstappen et al. |
| 6,641,708 | B1 | 11/2003 | Becker et al. |

(Continued)

FOREIGN PATENT DOCUMENTS

| | | |
|---|---|---|
| WO | 03035909 A2 | 5/2003 |
| WO | 2006098696 A1 | 9/2006 |

OTHER PUBLICATIONS

Guo, P. et al. Microfluidic capture and release of bacteria in a conical nanopore array. Lab Chip. vol. 12, p. 558-561, 2012, published online Nov. 2011.

(Continued)

*Primary Examiner* — Lisa Cook
(74) *Attorney, Agent, or Firm* — Jeffrey Schox; Ivan Wong

(57) ABSTRACT

A system and method for capturing and analyzing cells comprising: a fluid delivery module; a reservoir configured to receive a biological sample including a target cell population and at least one fluid from the fluid delivery module; a manifold configured to receive and distribute the biological sample and at least one fluid from the reservoir into a cell capture device; a waste chamber configured to couple to the manifold; and a pump configured to couple to the waste chamber. In embodiments of the system configured to promote further purification of captured cells, the system can further comprise a magnet that enables further separation of captured cells from undesired sample materials. The system can additionally further comprise a heater configured to heat at least one fluid and/or biological sample, and a cell capture device configured to couple to the manifold, in order to facilitate capture of the target cell population.

10 Claims, 17 Drawing Sheets

(56) References Cited

U.S. PATENT DOCUMENTS

| | | |
|---|---|---|
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,861,259 B2 | 3/2005 | Columbus |
| 6,960,449 B2 | 11/2005 | Wang et al. |
| 7,035,170 B2 | 4/2006 | Narayanaswami et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte De et al. |
| 7,332,288 B2 | 2/2008 | Terstappen et al. |
| 7,439,062 B2 | 10/2008 | Bhatt et al. |
| 7,449,558 B2 | 11/2008 | Yao et al. |
| 7,449,778 B2 | 11/2008 | Sander |
| 7,507,528 B2 | 3/2009 | Albert et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,175,371 B2 | 5/2012 | George et al. |
| 8,186,913 B2 | 5/2012 | Toner et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 9,174,216 B2 * | 11/2015 | Handique .......... G01N 35/0098 |
| 2002/0119482 A1 | 8/2002 | Nelson et al. |
| 2002/0192808 A1 | 12/2002 | Gambini et al. |
| 2003/0138941 A1 | 7/2003 | Gong et al. |
| 2004/0160599 A1 | 8/2004 | Hamamatsu et al. |
| 2004/0229349 A1 | 11/2004 | Daridon |
| 2004/0248318 A1 | 12/2004 | Weinberger et al. |
| 2005/0001176 A1 | 1/2005 | Loney et al. |
| 2005/0118640 A1 | 6/2005 | Kureshy et al. |
| 2006/0128006 A1 | 6/2006 | Gerhardt et al. |
| 2007/0111302 A1 | 5/2007 | Handique et al. |
| 2008/0014589 A1 | 1/2008 | Link et al. |
| 2008/0068588 A1 | 3/2008 | Hess et al. |
| 2008/0182273 A1 | 7/2008 | Hansen et al. |
| 2008/0206751 A1 | 8/2008 | Squirrell et al. |
| 2009/0061450 A1 | 3/2009 | Hunter |
| 2009/0081773 A1 | 3/2009 | Kaufman |
| 2009/0141593 A1 | 6/2009 | Taha |
| 2009/0153844 A1 | 6/2009 | Peter et al. |
| 2009/0317836 A1 | 12/2009 | Kuhn et al. |
| 2010/0120077 A1 | 5/2010 | Daridon |
| 2010/0210009 A1 | 8/2010 | Willson et al. |
| 2010/0304485 A1 | 12/2010 | Karnik et al. |
| 2010/0304978 A1 | 12/2010 | Deng et al. |
| 2011/0045994 A1 | 2/2011 | Voldman et al. |
| 2011/0117634 A1 | 5/2011 | Halamish et al. |
| 2011/0143964 A1 | 6/2011 | Zhou et al. |
| 2011/0227558 A1 | 9/2011 | Mannion et al. |
| 2012/0071355 A9 | 3/2012 | Cooney |
| 2012/0129190 A1 | 5/2012 | Chiu et al. |
| 2012/0156675 A1 | 6/2012 | Lueerssen et al. |
| 2012/0194805 A1 | 8/2012 | Ness et al. |
| 2013/0244906 A1 | 9/2013 | Collins |
| 2014/0173443 A1 | 6/2014 | Hawkins et al. |
| 2015/0089359 A1 | 3/2015 | Brisebois |
| 2015/0160931 A1 | 6/2015 | Glazer et al. |

OTHER PUBLICATIONS

Lindstrom, Sara (Royal Institute of Technology, Stockholm, Sweden, 2009, pp. 1-80).

Sugio et al. (Sensors and Actuators, B99, 2004, pp. 156-162).

* cited by examiner

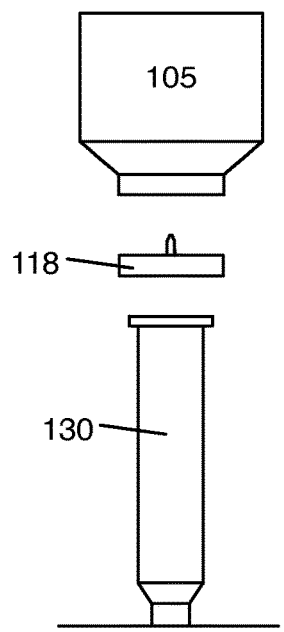
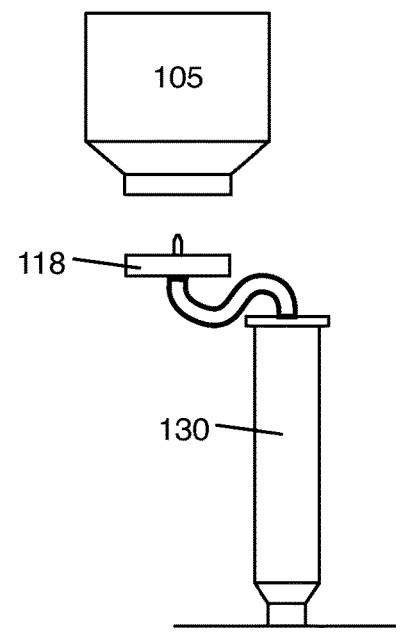
FIGURE 4A                FIGURE 4B
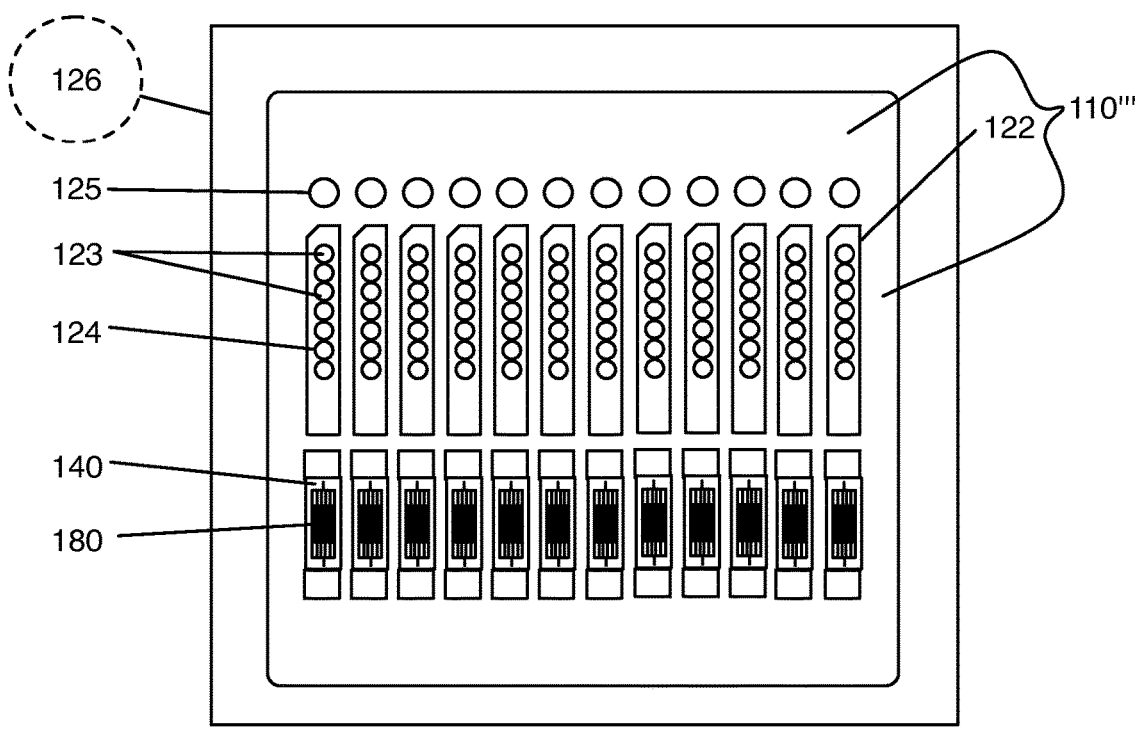
FIGURE 5

Top View

SYSTEM AND METHOD FOR CAPTURING AND ANALYZING CELLS

CROSS-REFERENCE TO RELATED APPLICATIONS

This application is a continuation of co-pending U.S. application Ser. No. 14/208,298, filed 13 Mar. 2014, which claims the benefit of U.S. Provisional application Ser. No. 61/894,150, filed on 22 Oct. 2013, U.S. Provisional application Ser. No. 61/829,528, filed on 31 May 2013, and U.S. Provisional application Ser. No. 61/779,049, filed on 13 Mar. 2013, which are all incorporated herein in their entirety by this reference.

TECHNICAL FIELD

This invention relates generally to the cellular analysis field, and more specifically to a new and useful system and method for capturing and analyzing cells.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting systems are becoming highly desirable. However, preexisting cell capture systems suffer from various shortcomings that prevent widespread adoption for cell-specific testing. For example, flow cytometry requires that the cell be simultaneously identified and sorted, and limits cell observation to a single instance. Flow cytometry fails to allow for multiple analyses of the same cell, and does not permit arbitrary cell subpopulation sorting. Conventional microfluidic devices rely on cell-specific antibodies for cell selection, wherein the antibodies that are bound to the microfluidic device substrate selectively bind to cells expressing the desired antigen. Conventional microfluidic devices fail to allow for subsequent cell removal without cell damage, and only capture the cells expressing the specific antigen; non-expressing cells and cells with a phenotypic transition, which could also be desired, are not captured by these systems. Cellular filters can separate sample components based on size without significant cell damage, but suffer from clogging and do not allow for specific cell identification, isolation, and retrieval.

Thus, there is a need in the cellular analysis field to create a new and useful system and method for capturing and analyzing cells. This invention provides such a new and useful system and method.

BRIEF DESCRIPTION OF THE FIGURES

FIGS. 4A and 4B show variations of a portion of a system for capturing and analyzing cells;

FIG. 5 depicts another variation of a portion of a system for capturing and analyzing cells;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1A:
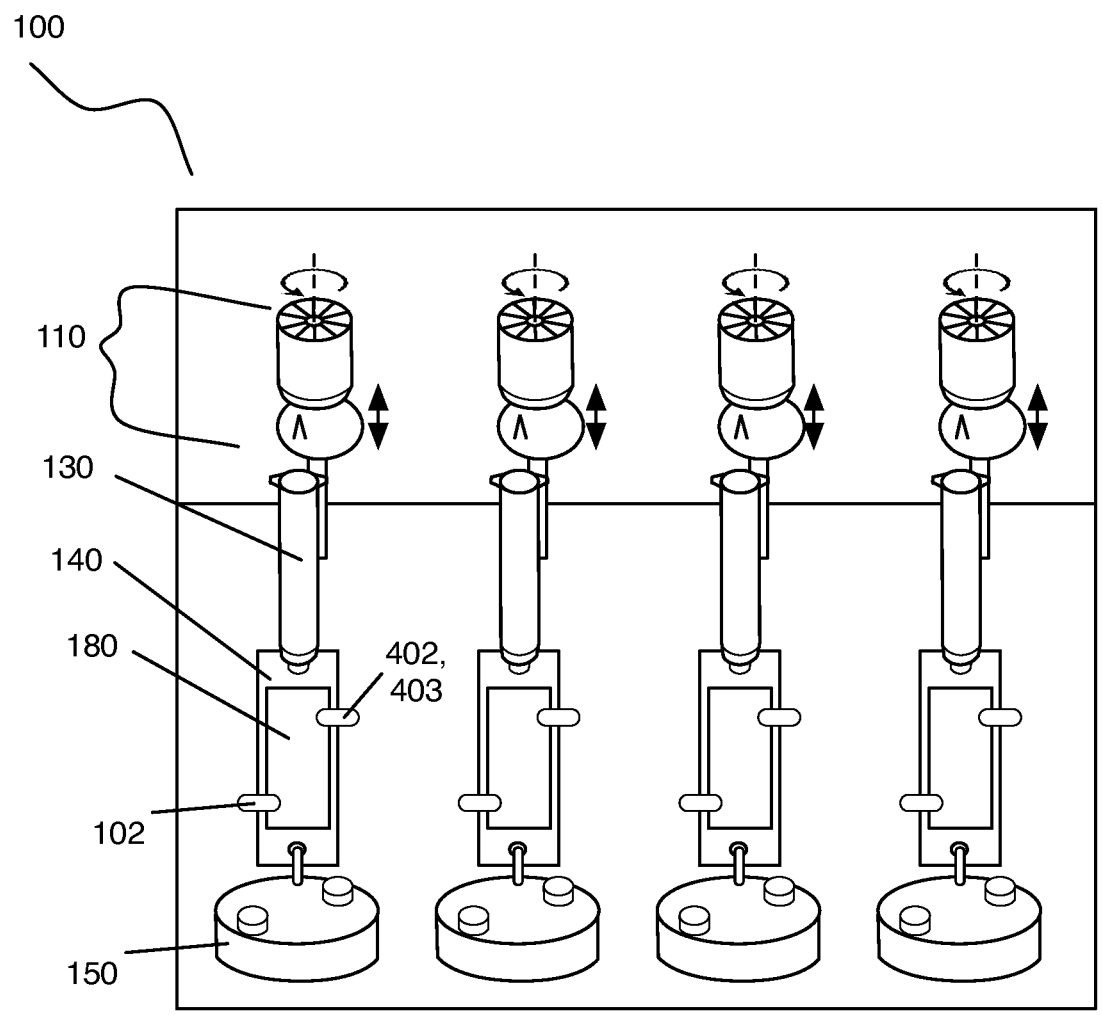
FIGS. 1A-1C depict an embodiment of a system for capturing and analyzing cells.
Figure 1B:
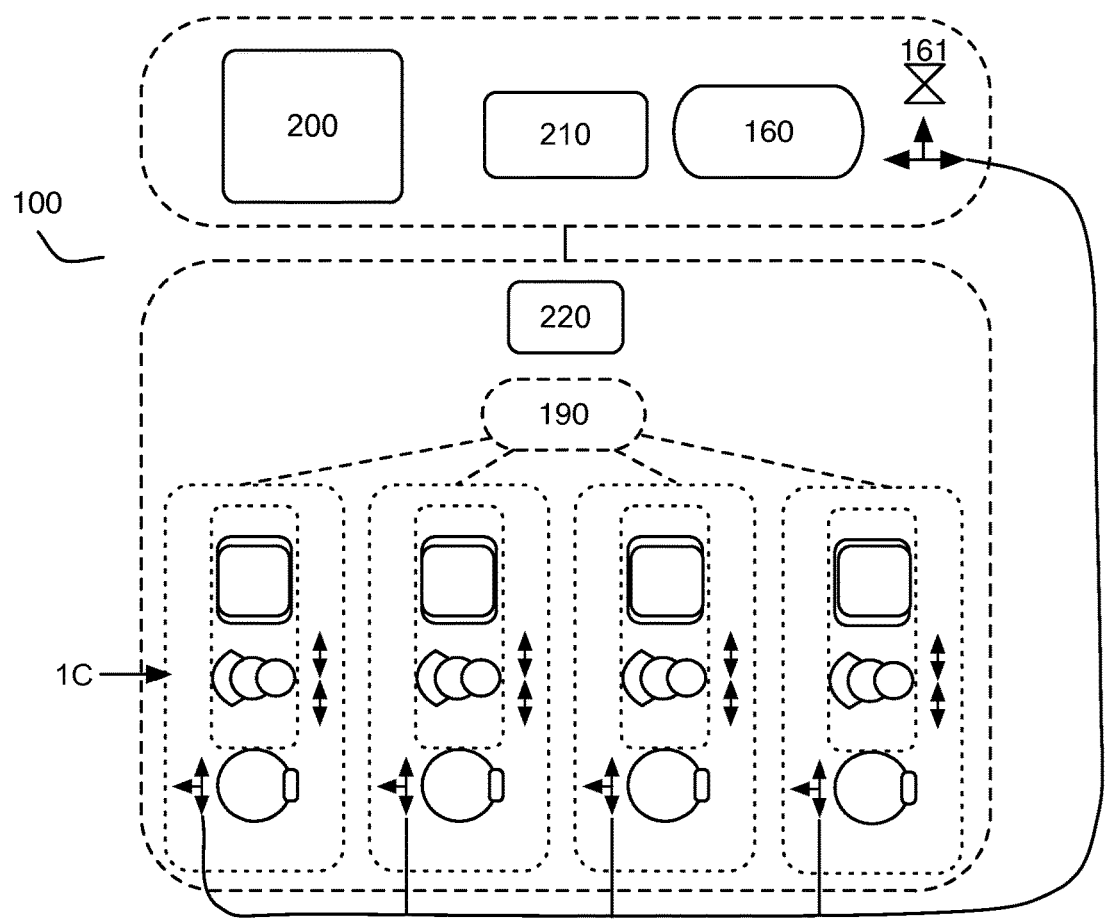
Figure 1C:
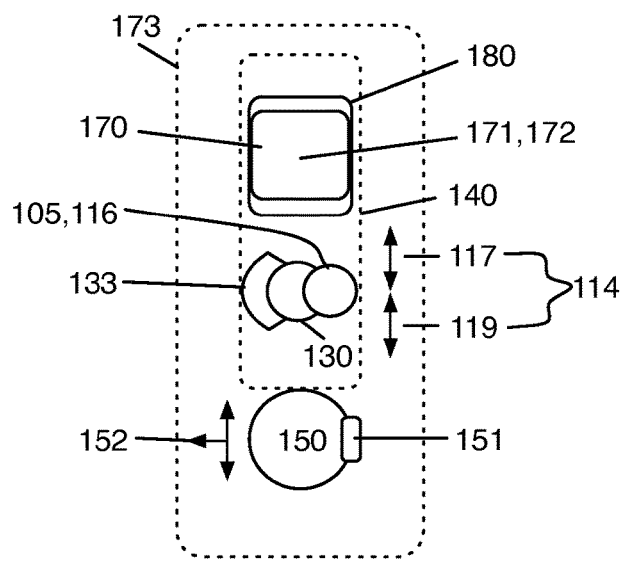

As shown in FIGS. 1A-1C, an embodiment of a system 100 for capturing and analyzing cells comprises: a fluid delivery module 110; a reservoir 130 configured to receive a biological sample including cells and at least one fluid from the fluid delivery module 110; a manifold 140 configured to receive and distribute the biological sample and at least one fluid from the reservoir iso; a waste chamber 150 configured to couple to the manifold 140; and a pump 160 configured to couple to the waste chamber 150. In embodiments of the system 100 configured to promote further purification of captured cells, the system 100 can further comprise a magnet 165 that enables further separation of captured cells from undesired sample materials. The system 100 can additionally further comprise a heater 170 configured to heat at least one fluid and/or biological sample, a cell capture device 180 configured to couple to the manifold 140, a bubble removal module 190, a processor 200, a data acquisition module 210, and a tag identifying system 220. The system 100 is preferably used to receive, capture, and process at least one biological sample including cells of interest, and can further be used to facilitate analysis of the captured cells of interest. The system 100 can be configured to facilitate real-time cell tracking, viable cell retrieval, and selective downstream molecular testing, within a cell capture device 180, such as a microfluidic chip, or off-chip. The system 100 preferably achieves individual cell capture without antibody coated chambers or biomagnetic tagging, and preferably maintains the cell viability throughout capture and retrieval. In a specific embodiment, the system 100 can be used to capture and analyze circulating tumor cells (CTCs) from clinical samples (e.g., blood, urine, cerebrospinal fluid, disseminated fine needle biopsies, cystic fluids, etc.), but in other embodiments can be used to capture and analyze any other suitable cell of possible interest.

1.1 System—Fluid Delivery Module

The fluid delivery module 110 functions to contain and deliver at least one fluid to the reservoir 130, in order to facilitate capture and/or analysis of cells within a biological sample. Preferably, the fluid delivery module 110 comprises a cartridge 105 having a set of chambers 111, each chamber 112 in the set of chambers configured to contain a fluid of a set of fluids to facilitate capture and/or analysis of cells. The cartridge 105 can be cylindrical, conical, frustoconical, prismatic, pyramidal, or of any other suitable morphology. Each chamber 112 in the set of chambers 111 is preferably identical to the other chambers, but can alternatively be non-identical to other chambers based on fluid storage requirements (e.g., volume requirements, temperature requirements, light exposure requirements, pressure requirements). The set of fluids preferably comprises reagents including buffers (e.g., priming, wash, and permeabilization buffers), fixing solutions (e.g., pre-fixing and post-fixing solutions), and cocktails (e.g., lysis, inhibitor, primary antibody, and secondary antibody cocktails), and can additionally or alternatively comprise stains (e.g., fluorescent stains or histological stains) and any other suitable fluids for cell capture or analysis. In variations of the system 100 configured to further promote purification of captured cells by magnetic separation, the set of fluids can also comprise solutions of magnetic beads coupled with affinity molecules configured to bind to components of interest (e.g., undesired cells, fragments, waste products) within a biological sample. In one example, a chamber 112 can contain a solution of streptavidin-coated magnetic microparticles, configured to bind to CD45-bound white blood cells (WBCs). In alternative variations, the fluid delivery module 110 can comprise a single chamber configured to facilitate delivery of a single fluid or multiple fluids to facilitate capture and/or analysis of cells within a biological sample. In other variations, the chamber(s) of the fluid delivery module 110 can be replaced by any suitable fluid conduit(s).

The fluid delivery module 110 can comprise a seal 113, which functions to isolate a fluid within the fluid delivery module 110. In embodiments wherein the fluid delivery module 110 comprises a set of chambers 111, the seal can further function to isolate a fluid of a set of fluids within an individual chamber 112, and to prevent cross-contamination between fluids within chambers of the set of chambers 111, and to prevent evaporative loss during storage and shipment. Preferably, the seal is a puncturable seal comprising a metal foil or any other suitable material, which functions to provide access to at least one fluid within the fluid delivery module 110. However, the seal can alternatively be configured to be non-puncturable, while still facilitating delivery of a fluid to the reservoir 130. Furthermore, the seal 113 can be an element separate from the cartridge 105, or can additionally or alternatively be contiguous with the cartridge 105 (e.g., physically coextensive, of unitary construction. For instance, the seal 113 can include one or more substantially thin sections of the cartridge 105 that can be punctured to provide access to contents of a chamber 112. In one specific variation, a non-puncturable seal can be coupled to a fluid conduit coupled to a chamber of the fluid delivery module 110, wherein the fluid conduit facilitates transfer of a fluid to the reservoir 130.

The fluid delivery module 110 is preferably configured to be prepackaged with at least one fluid (e.g., reagent, buffer, cocktail, stain, magnetic particle solution, etc.) inside a chamber, which functions to facilitate capture and/or analysis of cells of interest according to a specific, pre-defined protocol. Alternatively, the fluid delivery module 110 can be prepackaged in an open or semi-open configuration, such that a user can transfer at least one fluid into at least one chamber 112 of the fluid delivery module 110 to facilitate capture and/or analysis of cells of interest according to a different protocol. Preferably, at least part of the fluid delivery module 110 is configured to be consumable, such that a portion of the fluid delivery module 110 can be disposed of after one use or multiple uses. Alternatively, the fluid delivery module 110 can be configured to be reusable, such that fluids can be repeatedly transferred to a reusable fluid delivery module 110 configured to transfer fluids to the reservoir 130.

In embodiments of the fluid delivery module 110 comprising a cartridge 105 having a set of chambers 111, each chamber is preferably configured to be isolated from other chambers and individually accessible, which functions to control delivery of a specific fluid to the reservoir 130. In a first variation, the fluid delivery module 110 comprises a set of chambers 111, and comprises at least one seal 113 configured to seal the set of chambers 111, thus isolating each chamber in the set of chambers from other chambers. The seal 113 in the first variation is a puncturable foil seal, such that puncturing the seal 113 at a chamber location provides access to the chamber 112. In an example of the first variation, each chamber is sealed at two locations and puncturing the seal at the two locations exposes the chamber to atmospheric pressure, facilitating delivery of a fluid within the chamber, through a location of puncture, to the reservoir 130 by means of hydrostatic pressure. In another example of the first variation, each chamber is sealed and puncturing the seal 113 at a puncture location, while providing a positive pressure at the puncture location (e.g., using a hypodermic needle, using a syringe pump, etc.) facilitates delivery of a fluid within the chamber to the reservoir 130. In yet another example of the third variation, each chamber is sealed and applying negative pressure at a chamber location (e.g., through a valve or an opening) facilitates delivery of a fluid within the chamber to the reservoir 130. Puncturing a seal, applying positive pressure, and/or applying negative pressure at a chamber can be performed manually, or can alternatively be performed automatically using an actuation system 114 configured to enable access to contents of chambers of the cartridge 105. The fluid delivery module 110 can alternatively facilitate individual access and/or isolation of a chamber 112 using any other suitable mechanism or combination of elements.

Figure 2A:
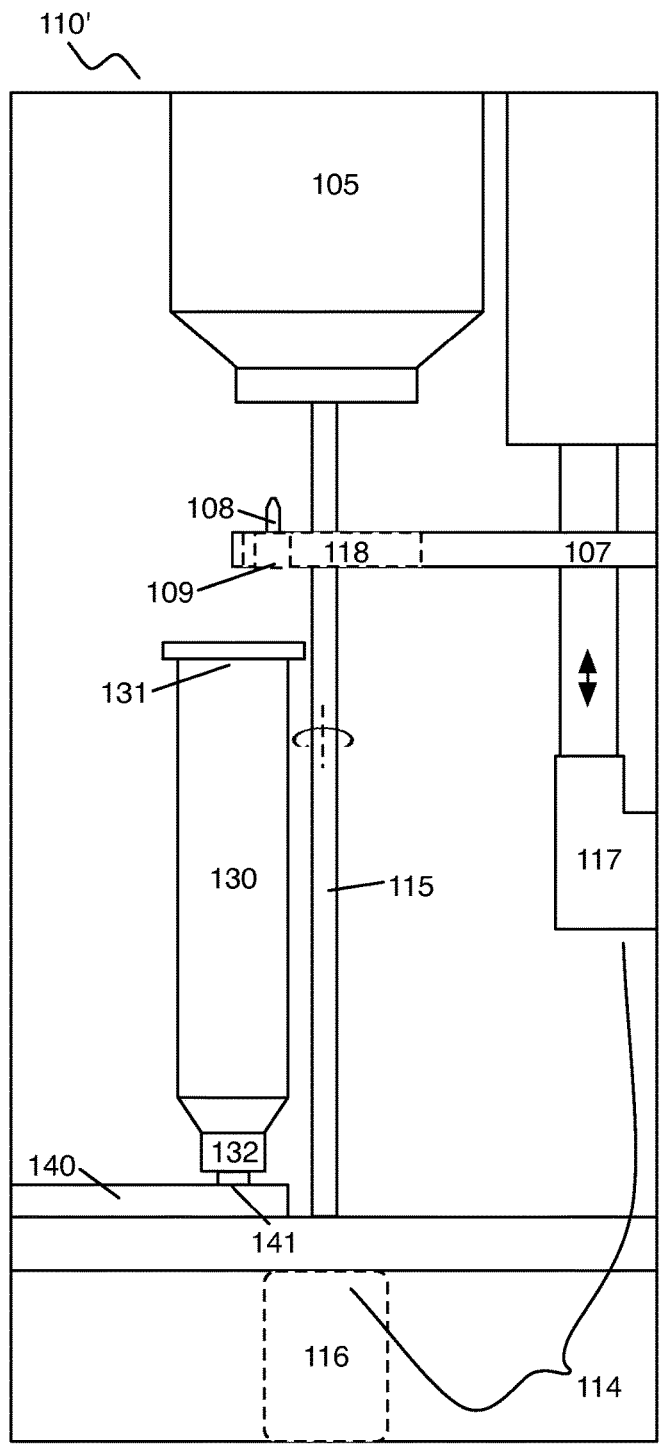
FIGS. 2A-2D depict a variation of a portion of a system for capturing and analyzing cells.
Figure 2B:
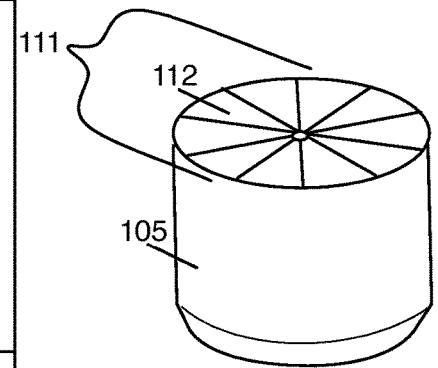
Figure 2C:
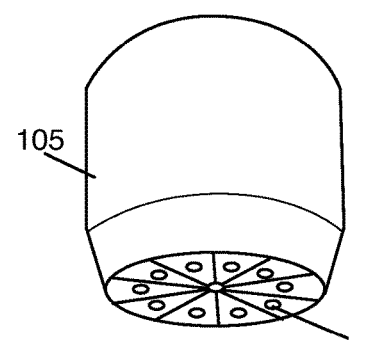
Figure 2D:
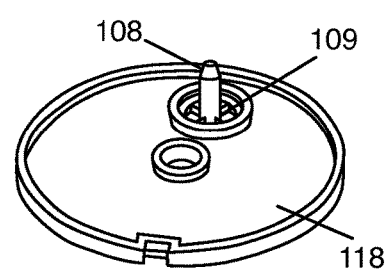

In a first specific example, as shown in FIGS. 2A-2D, the fluid delivery module 110' comprises a substantially cylindrical cartridge 105 comprising ten identical isolated chambers 112, each configured to contain a fluid or reagent to facilitate cell capture and/or analysis. In the first specific example, the cylindrical cartridge 105 can have one of an open configuration comprising open chambers, a semi-open configuration comprising open chambers and sealed chambers with prepackaged reagents, and a completely sealed configuration comprising sealed chambers with prepackaged reagents. In semi-open or sealed configurations, sealed chambers are sealed at two ends with a puncturable foil seal, and in open or semi-open configurations, open chambers are sealed at one end with a puncturable foil seal 113. Each of the ten chambers is has a volumetric capacity of 4-6 mL and has a wedge-shaped cross section that is substantially uniform along a majority of a 2" length. In the first specific example, the cartridge 105 has a bevel at an inferior region of the cartridge 105, as shown in FIGS. 2A-2C, in order to facilitate fluid flow toward an inferior region of the cartridge 105, proximal the seal 113.

The fluid delivery module 110' of the first specific example is also coupled to an actuation system 114 configured to individually access each chamber of the cylindrical cartridge, in order to facilitate automatic delivery of a fluid within each chamber to the reservoir 130. The actuation system 114 of the first specific example comprises a rotary shaft 115 driven by a stepper motor 116, wherein the rotary shaft is mounted to the cylindrical cartridge. In the first specific example, the rotary shaft 115 is mounted along an axis of rotation (e.g., a vertical axis of rotation) of the cartridge 105, such that the ten chambers 112 surround the axis of rotation. This configuration, along with the stepper motor 116, functions to allow determination of the positions of the ten chambers 112 as the cartridge 105 rotates during operation. The actuation system 114 of the first specific example also comprises a first actuator 117 configured to provide relative displacement between a first piercer 118 and the cartridge 105, in order to facilitate piercing of a seal 113 of a chamber 112 of the cartridge 105. In the first specific example, the first piercer 118 is situated inferior to the cartridge 105, and comprises a puncturing tip 108, that aligns with chambers 112 of the cartridge 105 in different rotational configurations of the cartridge 105, wherein the puncturing tip 108 is proximal to (e.g., concentric with) and coupled to (e.g., contiguous with) a boundary of an aperture 109 of the first piercer 118. As such, piercing of a seal 113 of the cartridge 105 at a chamber location, by way of the puncturing tip 108, facilitates flow of contents of the chamber(s) 112 through the aperture 109 of the first piercer 118 and into a reservoir 130 configured to receive chamber contents. In some variations, the puncturing tip 108 may also have an opening (e.g., an opening into a vertical channel, a slanted channel, or a channel with any other suitable orientation or path) to allow fluid to flow from the cartridge 105 to the reservoir 130. Additionally or alternatively, the structure of the puncturing tip 108 can extend below the surface of the first piercer 118 to allow fluid to drip in a guided fashion toward the reservoir 130.

In one variation of the first specific example, the actuation system 114 can displace the piercer 118 relative to the cartridge 105 (e.g., in a vertical direction, in a non-vertical inferior-superior direction) in order to drive the piercer 118 into a seal 113 of the cartridge 105. In this variation, the first piercer 118 can be coupled to a drip plate 107 that facilitates fluid delivery into the reservoir 130. In another variation of the first specific example, the actuation system 114 can displace the cartridge 105 relative to the piercer 118 (e.g., in a vertical direction, in a non-vertical inferior-superior direction), in order to drive the seal 113 of the cartridge toward the puncturing tip 108 of the piercer 118. In still other variations of the first specific example, the actuation system 114 can displace one or both of the cartridge 105 and the piercer 118 in any other suitable direction (e.g., vertical direction, a direction angularly displaced from a vertical direction, a horizontal direction) in order to enable piercing of a seal 113 of the cartridge 105. As such, in some variations of the first specific example, the cartridge 105 and/or the piercer 118 can be tilted away from a vertical or horizontal configuration. In tilted variations, fluid flow can be facilitated by gravity and/or application of positive or negative pressure to a chamber 112 of the cartridge 105.

Figure 3:
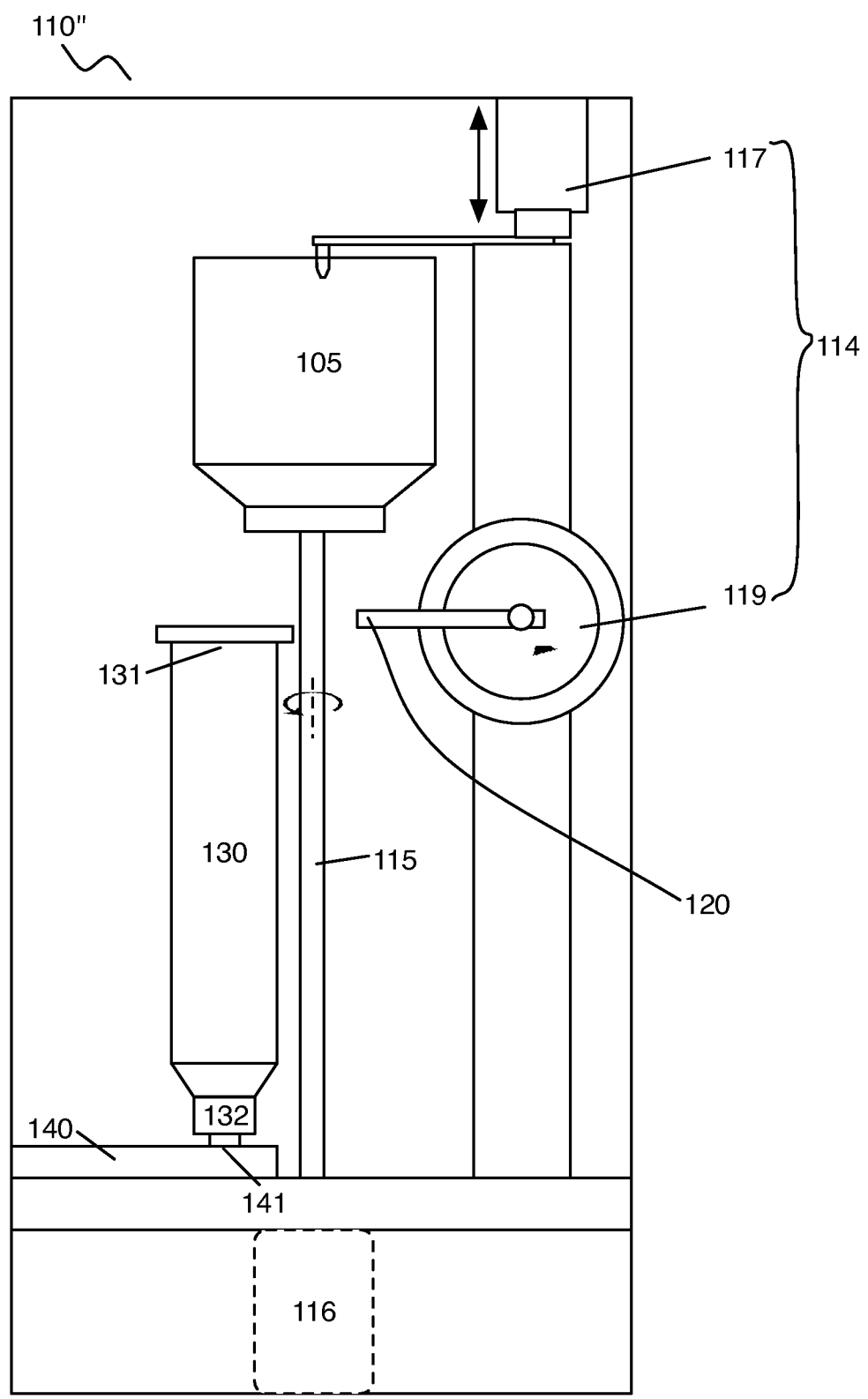
FIG. 3 shows another variation of a portion of a system for capturing and analyzing cells.

In a second specific example of the fluid delivery module 110", as shown in FIG. 3, the actuation system 114 comprises a first actuator 117 configured to drive a first piercer 118 to puncture a seal 113 at a first end of a chamber 112, and a second actuator 119 configured to drive a second piercer 120 configured to create an opening in a second end of the chamber 112. Puncturing the first end of the chamber 112 functions to vent the first end of the chamber 112 to atmospheric pressure, in order to facilitate fluid delivery from the chamber 112, and creating an opening in a second end of the chamber 112 functions to allow fluid within the chamber 112 to flow from the chamber 112, to the reservoir 130, due to hydrostatic pressure. In the second specific example, the first actuator 117 is a solenoid actuator configured to linearly displace the first piercer 118 relative to a chamber, and to drive the first piercer 118 into a puncturable foil seal at a first end of the chamber. The second actuator 119 is a rotary solenoid actuator configured to convert rotary motion into linear motion, such that the second piercer 120 coupled to the rotary solenoid actuator creates an opening in chamber through a puncturable foil seal 113 at a second end of the chamber 112. The first actuator 117 and the second actuator 119, however, can be replaced or supplemented by any suitable actuator (e.g., pneumatic or hydraulic actuator) or multiple actuators in variations of the second specific example. Furthermore, variations of the first and the second specific examples can include any suitable actuator(s) that enable a piercer 118, 120 to provide access to contents of a chamber 112. Similarly, the stepper motor 116 of the first and the second specific examples can be replaced or supplemented by any suitable actuator or element that enables determination of actuator position (e.g., an actuator coupled to a linear encoder). Thus, the actuation system 114 of the first and the second specific examples facilitates rotation of the cartridge 105 to position individual chambers 112 into alignment with at least one piercing element using a stepper motor, and facilitates puncturing of individual chambers using a subsystem of one or more actuators.

In both of the first and the second specific examples, the rotation of the cartridge positions a desired chamber 112 directly into alignment with (e.g., directly over) a reservoir 130 configured to receive and distribute contents of the chamber 112 into a manifold 140, as shown in FIG. 4A; however, in variations of first and the second specific examples, the cartridge 105, the chamber 112, and/or the reservoir may be out of alignment (e.g., offset), but fluidly coupled in any suitable manner to facilitate fluid flow from a chamber 112 to the reservoir 130. In one example, as shown in FIG. 4B, the reservoir 130 can be out of alignment with the chamber 112 of the cartridge, but coupled to a piercer 118 (or the chamber 112) using a fluid conduit (e.g., a flexible fluid conduit). Furthermore, still other variations of the first and the second specific examples can omit rotation of a cartridge 105, or can additionally or alternatively include translation of a cartridge (e.g., in X, Y, and/or Z directions) to align desired cartridge chambers 112 for delivery of processing fluids to a reservoir 130.

A third specific example of the fluid delivery module 110', as shown in FIG. 5, comprises a strip 122 comprising a set of wells 123, wherein each well 124 of the set of wells 123 is configured to individually contain a fluid for capture and/or analysis of cells of interest. The fluid delivery module 110" of the third specific example also comprises a sample container 125 configured to contain a biological sample including cells of interest. The sample container 125 and the set of wells 123 are isolated and accessible by a fluid delivery system 126 that functions to aspirate fluids and a biological sample from the strip 122 and the sample container 125, respectively, and to deliver fluids and a biological sample to a manifold 140 to facilitate cell capture and analysis. Variations of the first, the second, and the third specific examples can, however, include any other suitable elements or configurations that facilitate delivery of processing fluids to a reservoir 130 of the system 100.

The reservoir 130 comprises a reservoir inlet 131 and a reservoir outlet 132, and is coupled to the manifold 140. The reservoir 130 can further comprise a level sensor 133, as shown in FIG. 1C, configured to detect fluid level within the reservoir 130, which functions to prevent gas bubbles from entering the manifold 140. As such the level sensor can generate a signal upon detection of a trigger fluid level (e.g., a low fluid level as a threshold), and transmit the signal to a processor configured to receive the signal and generate a command to control fluid delivery into the manifold based upon the signal. The command can be used to automatically stop fluid flow from the reservoir into the manifold, or can function to implement control of fluid flow in any other suitable manner. The reservoir 130 functions to receive a biological sample including cells of interest and at least one fluid from the fluid delivery module 110, and to deliver the biological sample and at least one fluid to the manifold 140 to facilitate cell capture and/or analysis. The reservoir 130 is preferably coupled to the manifold 140 at a manifold inlet 141, and in a specific example, as shown in FIG. 2A, couples to the manifold inlet 141 using a threaded male-female coupling configured to provide a hermetic seal.

As described above, in variations, positioning of the cartridge 105 preferably places a desired chamber 112 directly into alignment with (e.g., directly over) the reservoir 130; however, the cartridge 105, the chamber 112, and/or the reservoir can alternatively be out of alignment (e.g., offset) with each other, but fluidly coupled in any suitable manner to facilitate fluid flow from a chamber 112 to the reservoir 130. In one example, as shown in FIG. 4B, the reservoir 130 can be out of alignment with the chamber 112 of the cartridge, but coupled to a piercer 118 (or the chamber 112) using a fluid conduit (e.g., a flexible fluid conduit).

In a first variation, the reservoir 130 includes an opening to atmospheric pressure, such that fluid delivery from the reservoir in an inlet-to-outlet direction is enabled by negative pressure applied by a pump 160 coupled indirectly to the reservoir 130 by at least one of the manifold 140 and the waste chamber 150. In the first variation, the negative pressure applied can be reversed in order to facilitate flow in an outlet-to-inlet direction. In a second variation, the reservoir 130 may not include an opening to atmospheric pressure, but can alternatively be coupled to a pump configured to provide positive pressure and negative pressure at the reservoir 130, in order to facilitate flow in both an inlet-to-outlet direction and an outlet-to-inlet direction, respectively. In a specific example of the second variation, the reservoir 130 is coupled to a syringe pump configured to provide positive and negative pressure by manual pumping. Fluid delivery from the reservoir 130 to the manifold 140 can, however, be performed in any alternative suitable manner. In variations of the reservoir 130 comprising a level sensor 133, the level sensor 133 can be a load cell, an ultrasonic level sensor, or any suitable signal configured to generate a signal when fluid level in the reservoir 130 passes a certain threshold. Detection of the signal can then generate a response to stop fluid flow within the system 100 and/or a response to add more fluid to the reservoir, thus preventing gas bubbles from entering the manifold 140. In a specific example, the reservoir 130 has a volumetric capacity greater than 6 mL, is configured to couple to the manifold inlet 141 by a threaded male-female coupling, and comprises an opening to atmospheric pressure, wherein the opening can also couple to a syringe pump. In the specific example, the reservoir 130 further comprises an ultrasonic level sensor configured to generate a signal when fluid level in the reservoir 130 passes a certain threshold. Other variations of the system 100 can altogether omit the reservoir 130 and use a network of fluid delivery conduits, with or without valves, to deliver at least one fluid to the manifold.

The manifold 140 comprises a manifold inlet 141, a manifold outlet 142, and can additionally or alternatively include a set of openings 143. The manifold 140 functions to enable controlled delivery of specific fluids, from the reservoir 130 and/or fluid delivery module no, in order to facilitate capture and/or analysis of cells of interest. The manifold inlet 141 functions to receive a fluid from the reservoir 130 and/or fluid delivery module 110, the manifold outlet 142 is configured to deliver waste fluids to a waste chamber 150 or to facilitate bubble removal, and the set of openings 143 is configured to enable fluid transfer between the manifold 140 and a cell capture device 180. Preferably, the manifold inlet 141 is configured to couple to the reservoir 130 at the reservoir outlet 132, the manifold outlet 142 is configured to couple to the waste chamber 150 or an outlet reservoir 192, and the set of openings 143 is configured to couple to a cell capture device 180 for capturing and analyzing cells of interest. The manifold inlet 141, the manifold outlet 142, and the set of openings 143 are also preferably configured to be fluidically connected by a fluid network 104, such that any pressure differential along the fluid network facilitates fluid flow through at least a portion of the fluid network.

Preferably, the manifold 140 has a substantially rectangular footprint; however, the manifold 140 can alternatively be defined by any other suitable morphology (e.g., ellipsoidal profile, polygonal profile, non-polygonal profile, etc.). Additionally, the manifold 140 is preferably of unitary construction as a single slab; however, in some variations, the manifold 140 can be composed of multiple pieces that are coupled together and/or maneuverable to facilitate coupling to a cell capture device 180. In one such variation, the manifold can include two components coupled by a hinge, that fold (e.g., as in a clamshell) to couple to the cell capture device 180 by way of the set of openings 143 (e.g., the set of openings can be defined at any of the components of the manifold 140). The manifold 140 preferably has a recessed region 103 configured to receive a cell capture device 180, wherein the recessed region 103 has a profile that facilitates reception of the cell capture device 180 and/or properly orients the cell capture device 180 at the manifold 140. However, the manifold 140 can alternatively not include a recessed region 103 to receive the cell capture device 180, and can facilitate proper reception and orientation of the cell capture device 180 in any other suitable manner (e.g., using guide rails, tabs, magnets, etc.).

Figure 6:
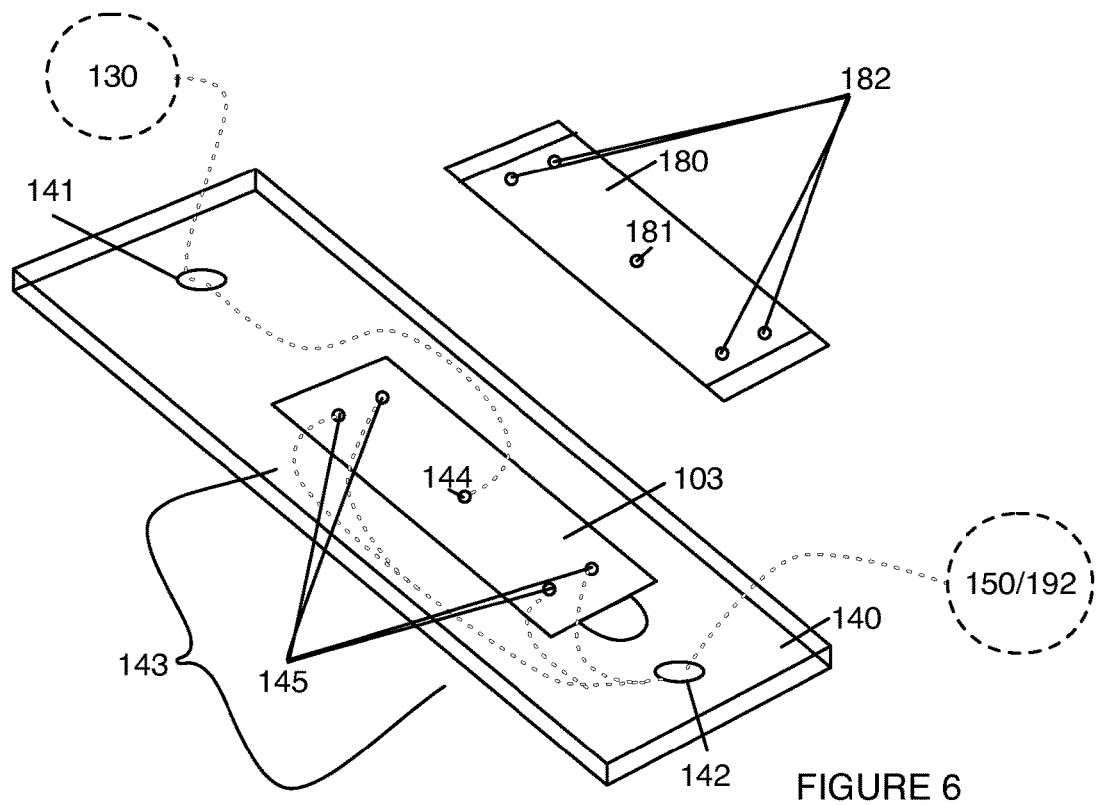
FIG. 6 depicts a variation of a manifold in a system for capturing and analyzing cells.

Preferably, the manifold inlet 141, the manifold outlet 142, and the set of openings 143 are defined at a first broad surface of the manifold 140 (e.g., an upward facing surface of the manifold 140), as shown in FIG. 6; however, the manifold inlet 141, the manifold outlet 142, and/or the set of openings 143 can be defined at any other suitable surface(s) of the manifold 140 (e.g., a downward facing surface of the manifold 140, at multiple surfaces of the manifold). In one variation, the manifold inlet 141 and the manifold outlet 142 are defined proximal to a periphery of a broad surface of the manifold 140, with the set of openings 143 defined at a central region of the broad surface of the manifold 140. Furthermore, in variations of the manifold 140 including a recessed region 103, the set of openings 143 are preferably defined at the recessed region 103, in order to facilitate fluid delivery to a cell capture device 180. In a specific example, the manifold inlet 141 and the manifold outlet 142 are defined proximal to opposing edges of a broad surface of the manifold 140, with the set of openings defined within a recessed region 103 of the manifold 140. However, in other variations, the set of openings 143, the manifold inlet 141, and the manifold outlet 142 can be defined with respect to the manifold 140 in any other suitable manner.

The set of openings 143 of the manifold 140 preferably comprises an inlet opening 144 and an outlet opening 145, wherein the inlet opening 144 is configured to couple to an inlet of a cell capture device 180, and wherein the outlet opening 145 is configured to couple to an outlet of the cell capture device. In one variation, the set of openings 143 can comprise more than one inlet opening 144 and/or more than one outlet opening 145, and in another variation, the set of openings 143 can comprise a single inlet opening 144 and a single outlet opening 145. Preferably, each opening of the set of openings 143 comprises a seated o-ring 149 configured to facilitate alignment and to provide a hermetic seal at each opening of the set of openings 143; however, the set of openings 143 can alternatively comprise any other suitable element (e.g., sealing putty, gasket, etc) configured to provide a hermetic seal at any opening of the set of openings 143. Other variations of the set of openings 143 may not be configured to provide a hermetic seal at each opening of the set of openings 143. As described above, the set of openings 143 is preferably coupled to the manifold inlet 141 and/or the manifold outlet 142 by a fluid network 104, wherein the fluid network 104 is preferably embedded within the manifold 140; however, in some variations, at least a portion of the fluid network can extend from, protrude from, couple to, and/or incorporate a surface of the manifold 140, in facilitating fluid flow with respect to a cell capture device 180 at the manifold 140.

Figure 7:
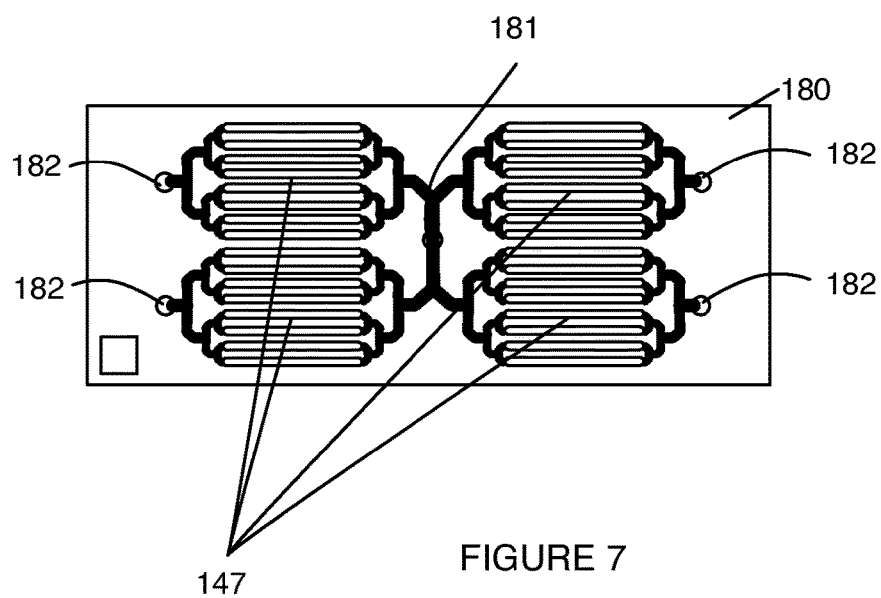
FIG. 7 shows an example of a cell capture device for capturing and analyzing cells.

In a specific example, as shown in FIG. 6, the manifold 140 comprises a manifold inlet 141 situated at a first edge of a broad surface of the manifold 140 and configured to couple to the reservoir 130 by a threaded male-female coupling to produce a hermetic seal, a manifold outlet 142 situated at a second edge (opposing the first edge) of the broad surface and configured to couple to the waste chamber 150 by a threaded male-female coupling to produce a hermetic seal, and a set of five openings 143 defined at a rectangular recessed region 103 and configured to couple to a cell capture device 180. The set of five openings comprises a single inlet opening 144 and four outlet openings 145. The single inlet opening is fluidically coupled to the manifold inlet 141, and configured to align with and couple to an inlet of the cell capture device 180. The four outlet openings 145 are fluidically coupled to the manifold outlet 142, and are each configured to align with and couple to a respective outlet of the cell capture device 180. The cell capture device 180 in the specific example thus comprises a set of four cell capture subarrays 147, as shown in FIG. 7, wherein an inlet of each cell capture subarray 147 is configured to couple to the common single inlet opening 144, and wherein an outlet of each cell capture subarray 147 is configured to couple to a respective one of the four outlet openings 145. In the specific example, o-rings 149 situated between the set of five openings of the manifold 140, and the inlets and outlets of the cell capture device 180 function to facilitate alignment, and to provide a hermetic seal between the manifold openings and the cell capture device inlet/outlets. Variations of the specific example can include any suitable number of inlet openings and/or outlet openings, fluidically coupled in any other suitable manner by a fluid network. Furthermore, variations of the specific example can include any suitable number and configuration of openings of the set of openings 143, in order to accommodate any other suitable cell capture device.

Figure 8:
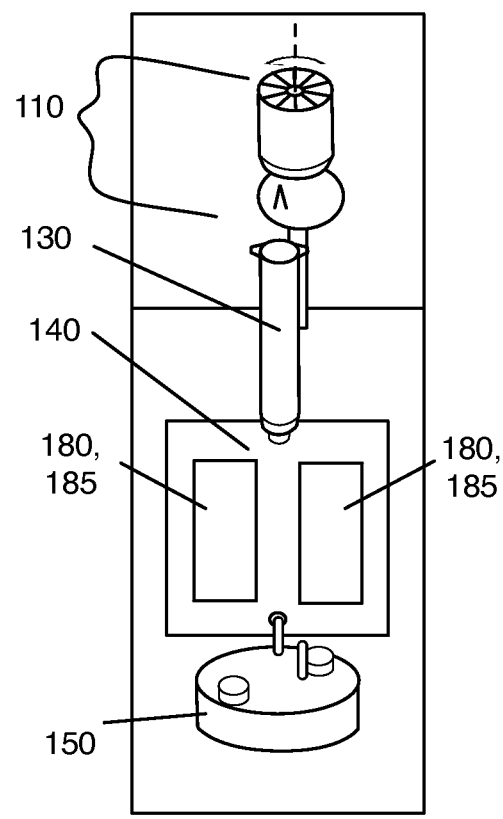
FIG. 8 depicts a variation of a portion of a system for capturing and analyzing cells.

As shown in FIG. 8, variations of the manifold 140 can be configured to couple to more than one cell capture device 180 or any other suitable imaging substrate. As such, a manifold 140 of the system 100 can include any one or more of the following features: more than one manifold inlet 141, more than manifold outlet 142, more than one set of openings 143, more than one recessed region 103, more than one fluid network 104 coupling a manifold inlet 141, a manifold outlet 142, and a set of openings 143, and any other suitable feature than facilitates fluid transfer to the cell capture device(s) 180. However, in these variations, the cell capture device(s) or imaging substrates can be configured to share any one or more of: a manifold inlet 141, a manifold outlet 142, a set of openings 143, a recessed region 103, a fluid network 104, and any other suitable feature of the manifold. Furthermore, a manifold 140 of the system 100 can be configured to accommodate multiple cell capture devices 180 or imaging substrates, wherein the cell capture devices/imaging substrates are non-identical and have different configurations of fluid inlets and outlets. For instance, a manifold can be configured to accommodate a cell capture device and a tissue biopsy imaging substrate, in series, in parallel, or in isolation from each other. In one variation, as shown in FIG. 8, a manifold 140 of the system 100 includes two recessed regions 103 defined at a broad surface of the manifold 140, each recessed region 103 including a set of openings 143 coupled by a fluid network 104. Each set of openings 143 in this variation couples by their respective fluid networks 104 to a shared manifold inlet 141 that receives processing fluid from a reservoir 130, and a shared manifold outlet 142, which couples to a waste chamber 150. As such, this variation of the manifold 140 accommodates two cell capture devices 180, configured to be seated at each of the two recessed regions 103, and configured to share a single reservoir 130 and waste chamber 150. In specific examples of this variation, the two cell capture devices 180 can be coupled in series (e.g., an outlet of one cell capture device 180 can be configured to feed into an inlet of the other cell capture device by the manifold 140), or in parallel. In still other variations, any suitable number of cell capture devices can be configured to couple in series and/or in parallel by one or more manifolds 140 of the system 100.

Figure 10A:
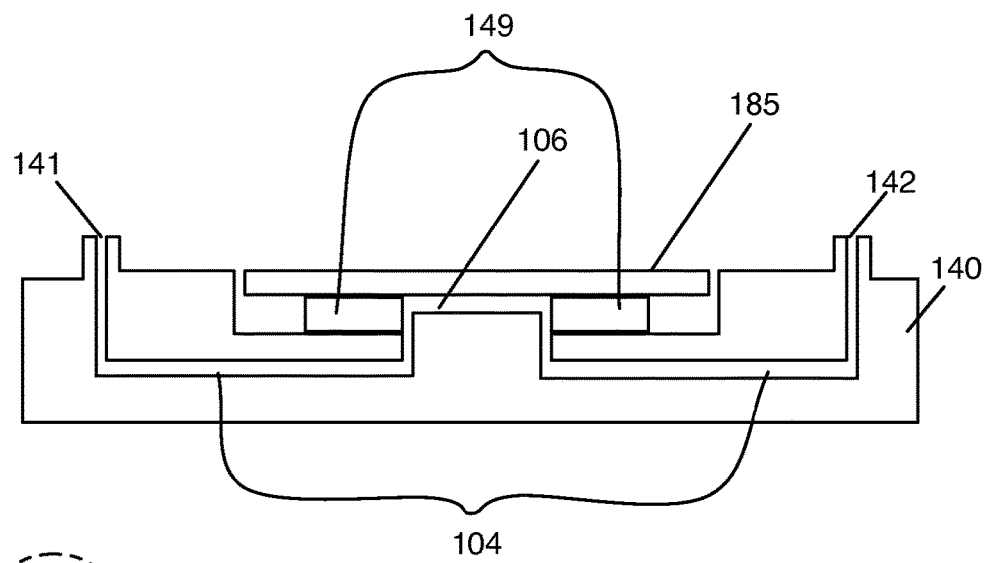
FIGS. 10A-10C depict variations of a portion of a system for processing and analyzing a tissue biopsy sample.
Figure 10B:
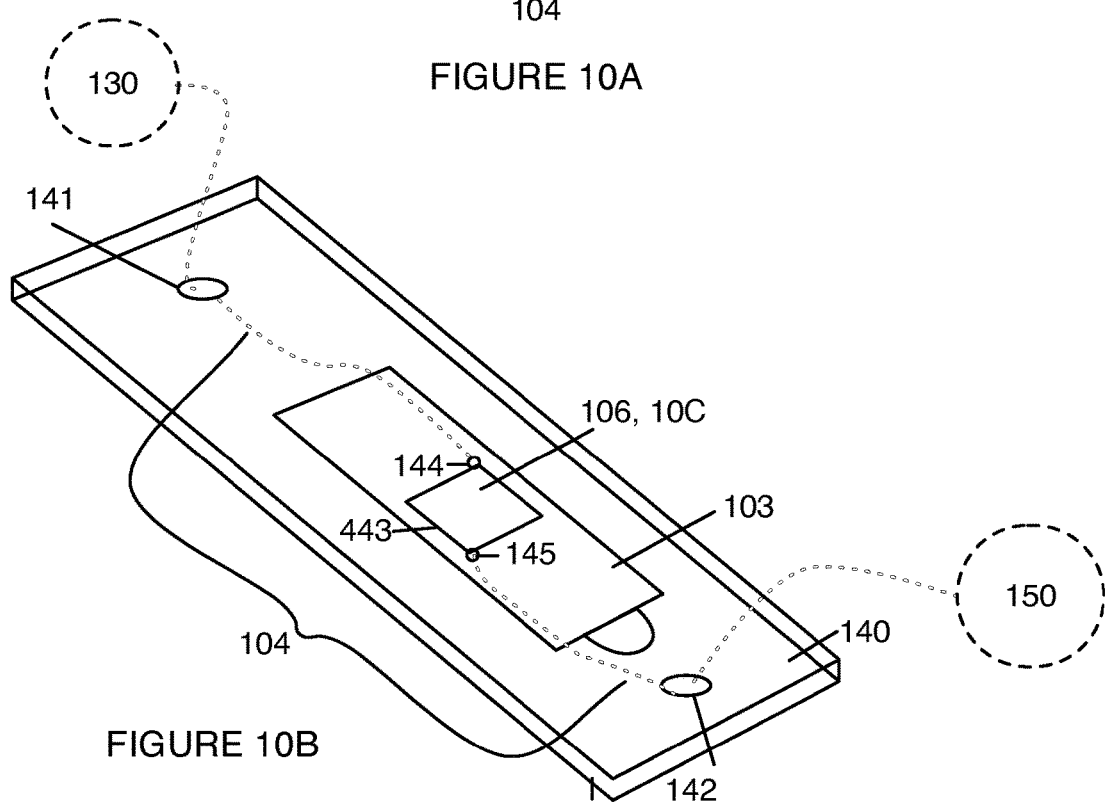
Figure 10C:
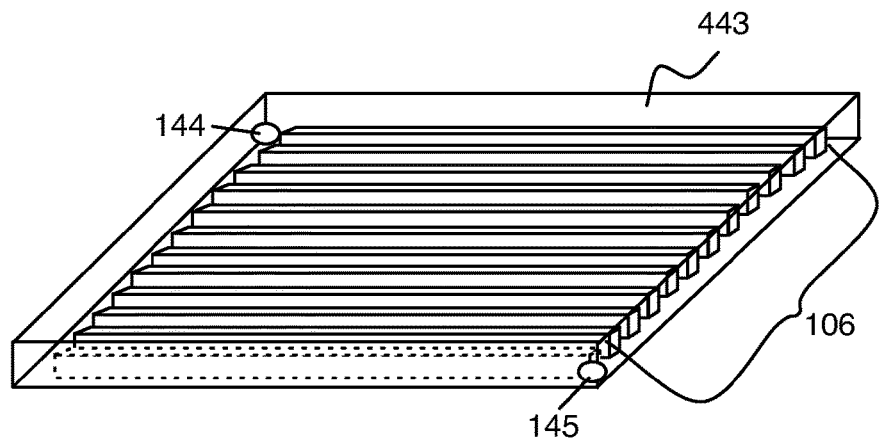

As shown in FIGS. 10A-10C, variations of the manifold 140 can additionally or alternatively be configured to receive a tissue biopsy imaging substrate 185 (e.g., tissue slide, microarray slide, tissue microarray slide), which functions to deliver at least one processing reagent from the reservoir 130 to a tissue sample at the tissue biopsy imaging substrate 185. As such, tissue samples at the tissue biopsy imaging substrate 185 can be processed, using the manifold 140 and the fluid delivery module 110, according to any one or more of the following assays: immunohistochemistry assay, DNA FISH on tissue assay, mRNA FISH assay, PCR on tissue assay, and any other suitable tissue-processing assay. In one such variation, the manifold 140 includes a manifold inlet 141, a manifold outlet 142, and a fluid network 104 including a set of microchannels 106 coupled between the manifold inlet 141 and the manifold outlet 142. The set of microchannels 106 preferably provide uniform fluid distribution at surface of the tissue biopsy imaging substrate 185, and in variations, can include a set of parallel microchannels separated by walls to define a corrugated surface, as shown in FIG. 10C. The walls in these variations can provide fluid isolation between individual microchannels, or can alternatively be of a height that enables fluid communication across individual microchannels upon coupling of the manifold 140 to the tissue biopsy imaging substrate 185. However, the set of microchannels 106 can alternatively be defined by any other suitable configuration (e.g., serpentine-shaped, boustrophedonic, contiguous, isolated, etc.). To enable fluid communication between the microchannels 106 of the fluid network 104, the manifold 140 in these variations also includes an opening 443 configured to provide fluid communication between the set of microchannels 106 and a surface of the tissue biopsy imaging substrate 185. Preferably, the opening 443 spans the set of microchannels 106; however, in other variations, the opening 443 may not span the set of microchannels 106, and/or the manifold 140 can include a set of openings 143 that enable fluid communication between the set of microchannels 106 and the surface of the tissue biopsy imaging substrate 185. As described above, hermetic sealing at the opening(s) 443, 143 can be provided by way of o-rings, sealants, gaskets, and/or any other suitable means of sealing an interface between the opening(s) and the surface of the tissue biopsy imaging substrate 185. Also described above, the opening(s) 443, 143 are preferably defined at a recessed region 103 of these variations of the manifold 140; however, the opening(s) 443, 143 may alternatively not be defined at a recessed region 103 of the manifold 140. In one specific example, as shown in FIGS. 10A-10C a manifold for receiving a tissue biopsy imaging substrate 185 (e.g., a glass slide with a 25 mm×75 mm profile) includes a manifold inlet 141 that couples to the reservoir 130, a manifold outlet 142 that couples to a waste chamber 150, a fluid network 104 including a set of parallel, non-isolated microchannels 106 fluidly coupled to the manifold inlet 141 and the manifold outlet 142, and a substantially square opening 443 with a gasket that enables fluid communication with hermetic sealing between the set of microchannels 106 and a surface of the tissue biopsy imaging substrate 185. In the specific example, the opening 143 and the set of microchannels 106 are defined at a recessed region 103 of a broad surface of the manifold 140, and the manifold inlet 141 and the manifold outlet 142 are defined at opposing peripheral regions of the broad surface of the manifold 140. Variations of the manifold inlet 141, the manifold outlet 142, the set of microchannels 106, and the opening 443 of the specific example can, however, be configured in any other suitable manner.

In order to facilitate sample processing and analysis, the cell capture device(s) 180 and/or the imaging substrate(s) (e.g., tissue biopsy imaging substrates) are preferably configured to be held in position at the manifold 140 by a restraining module 102, as shown in FIG. 1A. In one variation, the restraining module 102 includes at least one clamp 402 proximal to a region of the manifold 140 configured to receive the cell capture device(s)/imaging substrate(s), for instance, proximal to a recessed region 103 of the manifold 140. In one such variation, the clamp(s) 402 can be rotated or otherwise converted into a restraining configuration and out of a restraining configuration, to reversibly couple the manifold 140 to the cell capture device(s)/imaging substrate(s). In another variation, the restraining module 102 includes at least one magnet 403 configured to interact with another complementary magnet (e.g., at a cell capture device, etc.) in order to facilitate coupling of the manifold 140 to the cell capture device(s)/imaging substrate(s). The restraining module 102 can directly restrain the cell capture device(s)/imaging substrate(s), or can restrain the cell capture device(s)/imaging substrate(s) by way of a restraining plate 404 (e.g., the cell capture device can be coupled between the manifold 140 and the restraining plate 404). The restraining module 102 is preferably configured to provide a clamping pressure (e.g., uniform pressure, non-uniform pressure) between the manifold 140 and the cell capture device(s)/imaging substrate(s), thereby facilitating formation of hermetic seals at openings; however, the restraining module 102 can alternatively be configured to provide coupling between the manifold 140 and the cell capture device(s)/imaging substrate(s), without providing clamping pressure. Additionally, variations of the system 100 can alternatively omit the restraining module(s) 102 and instead, the cell capture device(s) 180 and/or the imaging substrate(s) can be positioned at the manifold(s) 140 without use of a restraining module 102.

Figure 9:
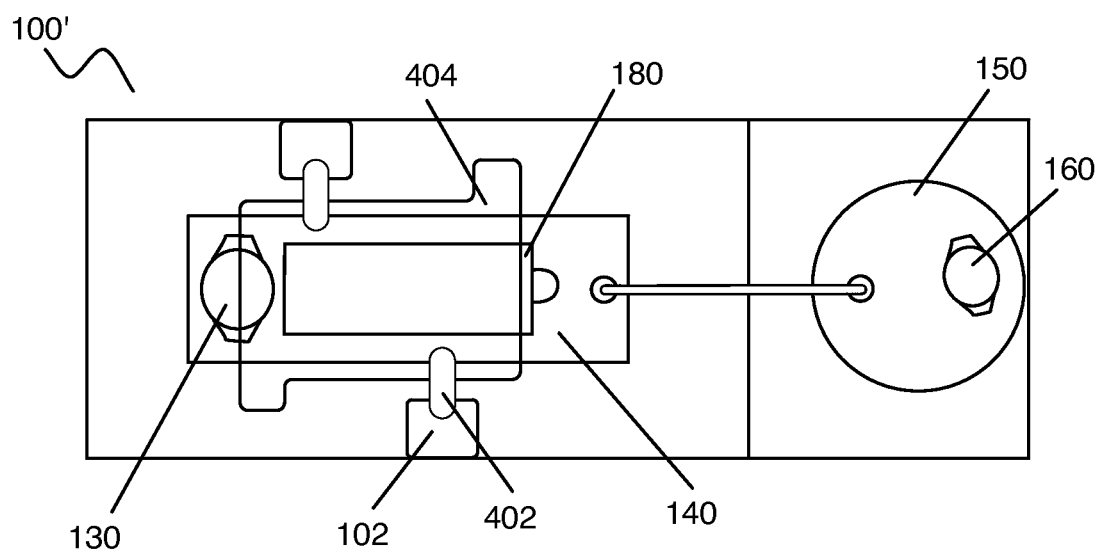
FIG. 9 depicts a manual variation of a system for capturing and analyzing cells.

The waste chamber 150 is configured to couple to the manifold 140 at the manifold outlet 142, and functions to receive a waste fluid that is transferred from a cell capture device 180, through an outlet opening 145, and through the manifold outlet 142. The waste chamber 150 can also be coupled to the pump 160, as shown in FIG. 9, which enables the waste chamber 150 to function as a pressure chamber that facilitates fluid flow throughout the system 100. Additionally, the waste chamber 150 can also comprise a level sensor 151, as shown in FIG. 1C, which functions to facilitate detection of a waste fluid level within the waste chamber 150. As such the level sensor 151 can generate a signal upon detection of a trigger fluid level (e.g., a low fluid level as a threshold), and transmit the signal to a processor configured to receive the signal and generate a command to control fluid delivery into the manifold (or out of manifold) based upon the signal. The command can be used to automatically stop fluid flow from the reservoir into the manifold, can be used to empty the waste chamber 150 (e.g., automatically, manually), or can function to implement control of fluid flow in any other suitable manner. Preferably, the waste chamber 150 is coupled to the manifold 140 in a manner that provides a hermetic seal at the manifold 140 and at the waste chamber 150, such that waste fluids do not leak at the manifold 140 or at the waste chamber 150. In variations wherein the waste chamber 150 is coupled to the pump 160, the waste chamber 150 is preferably a sealed vessel connected to the pump by a valve 152, such that the pump 160 can efficiently apply positive pressure and/or negative pressure, through the waste chamber, to other elements of the system 100. The waste chamber 150, however, may not be a sealed vessel. Furthermore, other configurations of the system 100 can comprise a waste chamber 150 that is not coupled to the pump 160, wherein the system 100 further comprises a pressure chamber that is coupled to the manifold 140 and to the pump 160 to provide positive pressure and/or negative pressure throughout at least a portion of the system 100. The system 100 can additionally or alternatively comprise any suitable configuration of elements to receive waste fluids and to drive biological samples and fluids throughout the system 100.

In a specific example, the waste chamber 150 is coupled to the manifold outlet 142 by a flexible tube, wherein a threaded male-female coupling provides a hermetic seal where the flexible tube couples to manifold outlet 142, and wherein the flexible tube is also coupled to the waste chamber 150. The waste chamber 150 in the specific example comprises a level sensor 151 configured to detect a waste level within the waste chamber 150, and to generate a signal when the waste level within the waste chamber 150 passes a certain threshold. The signal is then used to generate a response to empty the waste chamber to prevent backflow or system clogging. The waste chamber 150 in the specific example is a sealed vessel, coupled to the pump 160 by a valve 152. The valve 152 in the specific example is a multi-way valve, providing connections at least to the atmosphere, to the waste chamber 150, and to the pump 160, such that the waste chamber 150 can be solely connected to the pump 160 in a first configuration, or to the atmosphere in a second configuration.

The pump 160 is configured provide at least one of positive pressure and negative pressure, and functions to facilitate fluid flow through the system 100. Preferably, the pump 160 is configured to provide both positive pressure and negative pressure, such that fluid can flow in a forward direction and in a reverse direction within an element of the system 100. Flow in a forward direction preferably facilitates capture of cells of interest from a biological sample, and flow in a reverse direction preferably facilitates retrieval and/or analysis of cells of interest from the biological sample. Preferably, the pump 160 is configured to couple to the waste chamber 150 and comprises a multi-way valve 162 configured to provide a connection at least between the pump 160 and the atmosphere, and between the pump 160 and the waste chamber 150. The pump 160, however, can additionally or alternatively be coupled to any suitable element of the system to facilitate fluid flow, comprise a valve configured to provide any suitable alternative connection, and/or may not comprise a multi-way valve 162. In some variations, the pump 160 can also comprise a pressure sensor 161, which functions to enable measurement of a pressure provided by the pump 160. In one example, the pump 160 is a syringe pump, as shown in FIG. 9; however, the pump 160 can be any suitable pump configured to provide at least one of a positive pressure and a negative pressure to facilitate fluid flow within the system 100.

Figure 13:
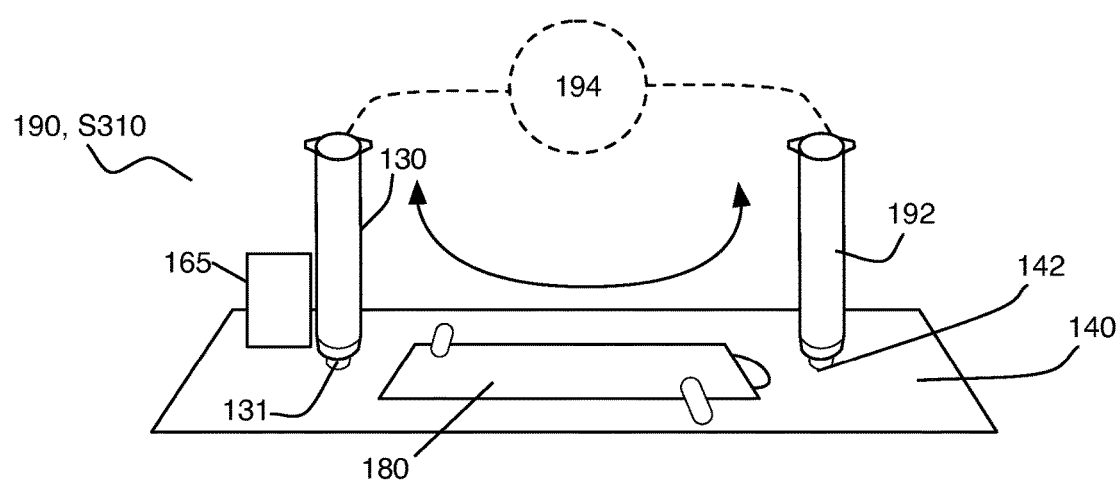
FIG. 13 shows a variation of a magnetic separation module of an embodiment of the system.

In embodiments of the system 100 configured to promote further purification of captured cells, the system 100 can further comprise a magnet 165 that enables separation of captured cells from undesired sample materials. The magnet 165, as shown in FIG. 13 is preferably a single magnet, but can alternatively be one of multiple magnets (e.g., lined up in parallel), in order to provide a greater magnetic flux to capture magnetically-bound particles. Preferably, the magnet 165 or group of magnets is coupled to a magnet holder of the system 100, wherein the magnet holder is configured stabilize the position of the magnet(s) 165 of the system 100 to provide experimental consistency. Additionally, the magnet 165 is preferably configured to be positioned proximal to the reservoir 130, such that purification of captured cells is facilitated within the reservoir 130 by a magnetic field provided by the magnet; however, in alternative variations, the magnet can be unfixed or fixed relative to any suitable element of the system. In an example, as shown in FIG. 13, the magnet 165 is a rectangular prism-shaped magnet 165 fixed to the manifold 140 proximal to the reservoir 130 and contacting a wall of the reservoir, such that particles of a sample bound to magnetic beads can be reversibly captured at a wall within the reservoir 130. In another example, the magnet can be configured to provide a magnetic field at the manifold 140, at the cell capture device 180, or at an outlet reservoir 192, such that magnetically-bound particles can be captured within at least one of the manifold 140, the cell capture device 180, and the outlet reservoir 192 during processing and/or purification.

In one variation, the magnet 165 or group of magnets comprises a permanent magnet, composed of a magnetized material (e.g., a ferromagnet) providing a substantially fixed magnetic field. In an alternative variation, the magnet 165 or group of multiple magnets comprises an electromagnet configured to provide a modifiable magnetic field, such that the intensity of the magnetic field can be adjusted, the polarity of the magnetic field can be reversed, and the magnetic field can be substantially removed upon removal of a current flowing within the electromagnet. The system 100 can, however, comprise alternative configurations and/or compositions of the magnet 165 in order to facilitating isolation, separation, and/or purification of particles within the biological sample using at least one of the reservoir 130, the manifold 140, and a cell capture device 180.

The system 100 can further comprise a heater 170, which functions to heat a biological sample containing cells of interest and/or a fluid to facilitate cell capture and analysis. The heater 170 can further function to facilitate reactions requiring high temperatures, such as for cell lysis, enzyme activations for probe hybridizations and thermocycling of biological sample mixtures for molecular diagnostic protocols, such as polymerase chain reaction (PCR). The heater 170 is preferably a thin heater configured to controllably heat the biological sample and/or fluid.

Figure 11A:
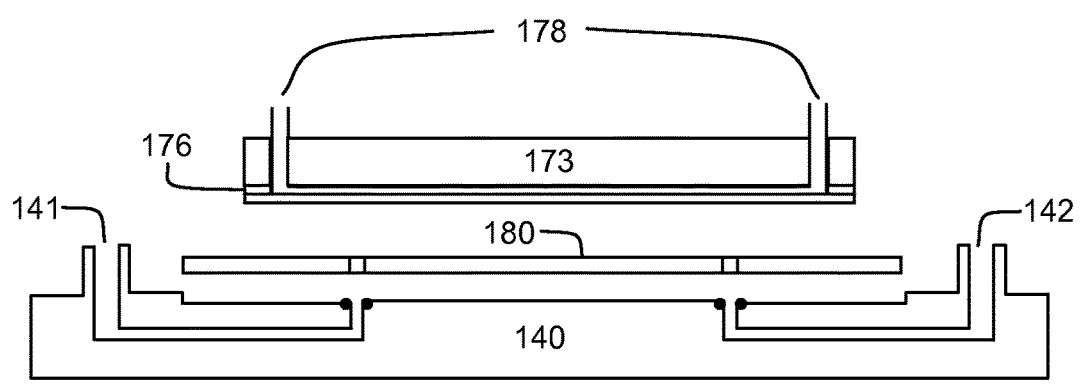
FIGS. 11A-11C show embodiments of a heater and plate for heating a biological sample and/or fluid.
Figure 11B:
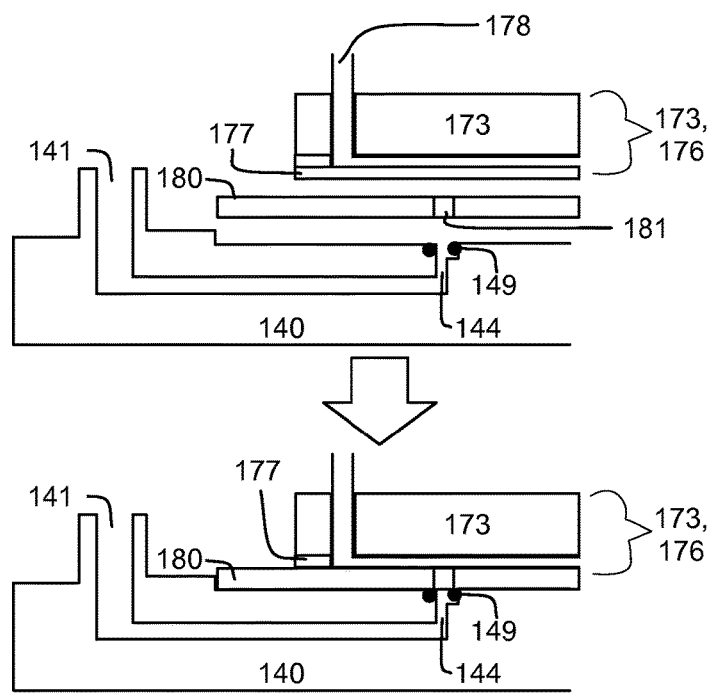
Figure 11C:
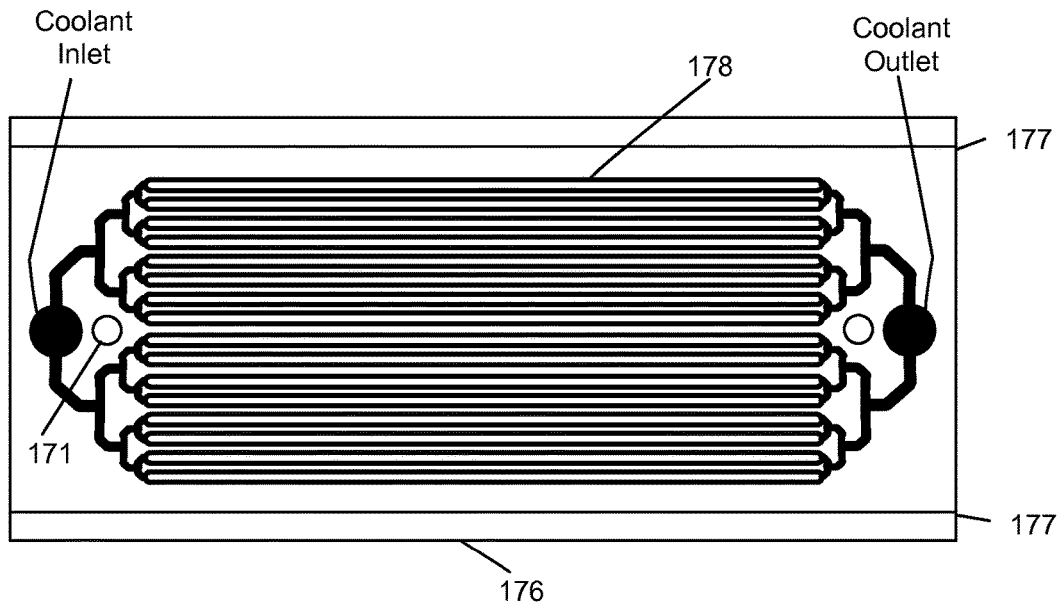

In a first variation, as shown in FIG. 11C, the heater 170 comprises a heat-conductive substrate 176 coupled to a heating element 177. In the first variation, the heat-conductive substrate 176 preferably houses the heating element 177; however, the heating element can alternatively be configured to contact a surface of the heat-conductive substrate 176. The heat-conductive substrate 176 can be composed of a conductive material (e.g., silicon, aluminum, copper, gold, silver), or any other suitable material for transferring heat from the heating element 177. Preferably, the heat-conductive substrate 176 maintains temperature uniformity over a heating surface with less than 1° C. variability over the heating surface; however, the heat-conductive substrate 176 can provide any suitable temperature profile over a heating surface. In the first variation, the heat-conductive substrate 176 preferably has a thin profile (e.g., has a dimension less than 4 mm thick), to reduce the energy required to heat the heat-conductive substrate to a specified temperature. The heat-conductive substrate can be further configured to provide cooling. In a specific example of the first variation, less than 10 or 20 Watts of power is required to heat the heat-conductive substrate 176 to a temperature of 100° C. from room temperature within an appropriate amount of time.

The heating element 177 of the first variation can be a wire or any suitable-shaped element (e.g., thin or thick film) configured to generate and transfer heat to the heat-conducting substrate. In an example, the heating element 177 is a nichrome wire, embedded within the heat-conductive substrate 176, and configured to generate heat by resistive heating (i.e., joule heating). The heater 170 in the example comprises two nichrome wires, as heating elements 177, located proximal to two long edges of the heat-conductive substrate 176; however, in variations of the example, the heater 170 can include any suitable number of heating elements 177 at any suitable location of the heat-conductive substrate 176. In the example, heat ramping is achieved by running currents of up to 1 ampere through the nichrome wire. In another example, the heating element 177 can comprise a heat-sinked power resistor, whereby heat is transferred from the heating element 177 through its integral heat sink to the heat-conductive substrate. In variations of this example, the system 100 can comprise multiple heating elements 177, which can be arranged in series, in parallel, or any combinations of series and parallel depending on any one or more of: a desired heating output (e.g., desired output in watts), a desired current capacity of associated controller circuitry, and any other suitable electrical specification parameter.

In a second variation, heating can be provided through one face of a plate-shaped heater. In an example of the second variation, heating through one face can be accomplished by using a plate-shaped resistance heater that has one exposed face and thermal insulation covering all other faces. In another example of the second variation, heating can be provided through one face of a heater by using a Peltier heater. In a variation of the heater 170 using a Peltier heater, the heater 170 comprises a thermoelectric material, and produces different temperatures on opposite faces of the heater 170 in response to a voltage difference placed across the thermoelectric material. Thus, when a current flows through the Peltier heater, one face of the Peltier heater lowers in temperature, and another face of the Peltier heater increases in temperature. The system 100, however, can further comprise any other suitable heater 170 configured to heat a biological sample and/or a fluid.

The heater 170 is preferably coupled to a temperature control module 171, such that heat can be controllably provided by the heater 170. The temperature control module 171 can comprise a temperature sensor 172, or any other suitable element configured to facilitate temperature control. For example, the temperature sensor 172 can couple to a heat-conductive substrate 176, to a heating element 177, or to a plate-shaped heater. Temperature control can be enabled using pulse-width modulation through fuzzy logic control, a proportional-integral-differentiation algorithm, or any other suitable means. Temperature control can be provided to a resolution of 1° C., or any other suitable resolution given the application.

As shown in FIGS. 11A-11C, the heater 170 is also preferably coupled to a plate 173, wherein the plate 173 is configured to facilitate coupling of the manifold 140 to a cell capture device 180. In one variation, the heater 170 is coupled to one surface of the plate 173, and in another variation, the heater 170 is embedded within the plate 173. The plate 173 is preferably configured to facilitate heat transfer between the heater 170 and a cell capture device 180, such that a biological sample and/or a fluid within the cell capture device 180 can be appropriately heated. In some variations, cell capture device 180 can be clamped between the plate 173 and the manifold 140, which functions to facilitate alignment and formation of hermetic seals between the set of openings 143 of the manifold 140 and the cell capture device 180, using, for example, an o-ring 149. As shown in FIG. 11C, the plate 173 can be further configured to provide conductive cooling through a fluid path 178; however, cooling may not be provided, or can be provided using any other suitable element (e.g., a fan blower coupled to provide forced air cooling as necessary). In variations wherein the plate 173 is configured to provide cooling, cooling can be enabled by flowing a coolant (e.g., water, oil, air, composite liquid) through a fluid path 178, and controlled using a controlled fluid pump.

In a specific example of the plate 173 and heater 170, as shown in FIGS. 11B-11C, the plate 173 couples to the heat-conducting substrate 176 comprising a pair of embedded nichrome wires, and forms a fluid path 178 configured to provide conductive cooling. The nichrome wires of the specific example are located at the periphery along opposing long edges of the heat-conductive substrate 176, and the fluid path 178 forms a network with microfluidic channels (100-500 μm wide and 50-500 μm deep) configured to transmit coolant. The fluid path 178 forms an inlet and an outlet passing through the plate 173.

The system 100 can also further comprise a cell capture device 180, which functions to enable capture and analysis of cells of interest within a biological sample. The cell capture device 180 is preferably the cell capture device described in U.S. application Ser. No. 13/557,510, entitled "Cell Capture System and Method of Use" or that described in U.S. application Ser. No. 14/163,153, entitled "System and Method for Capturing and Analyzing Cells", which are both incorporated in their entirety herein by this reference. However, the cell capture device 180 can alternatively be any other suitable device configured to facilitate capture and analysis of cells of interest within a biological sample. In a specific example, the cell capture device 180 is a microfluidic chip with a 1"×3" footprint to adhere to glass slide dimensional standards, such that the microfluidic chip can be handled and manipulated by other systems. In the specific example, as shown in FIG. 7, the cell capture device 180 comprises a single inlet 181, four outlets 182, and four subarrays 147, such that each subarray is coupled to the single inlet and one of the four outlets. The four subarrays 147 comprise 56,400 pores to capture cells of interest for later retrieval and analysis. The single inlet and the four outlets are configured to align with the set of openings 143 of the manifold 140, and the microfluidic chip of the specific example is configured to be clamped between the manifold 140 and a plate coupled to a heater 170. The microfluidic chip of the specific example is also composed of an injected molded material with an appropriately high glass transition temperature to handle molecular diagnostic protocols, including FISH and PCR. The microfluidic chip is also composed of a low-autofluorescence material that is optically transparent, to facilitate analyses involving light transmission and detection.

Figure 12:
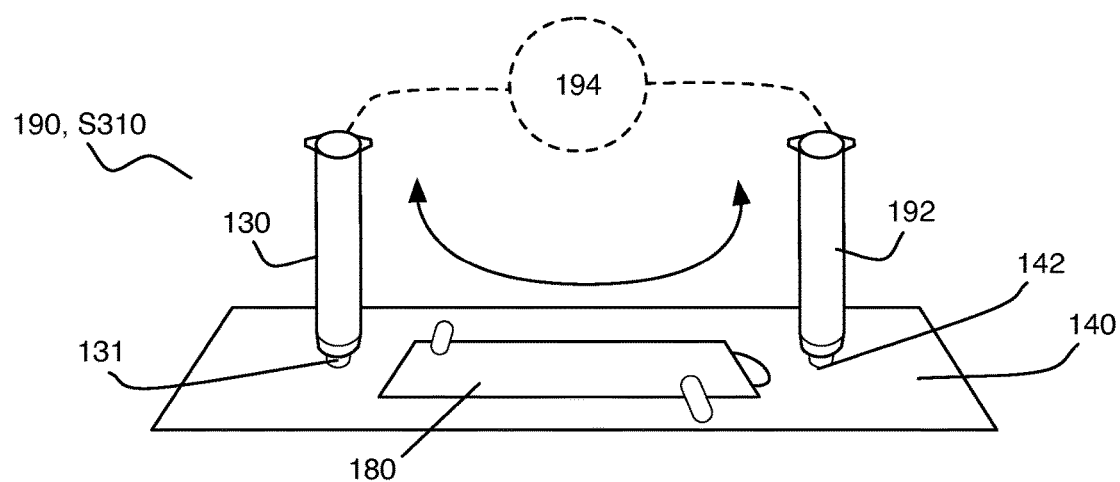
FIG. 12 shows a variation of a bubble removal module of an embodiment of the system.

The system 100 can also further comprise a bubble removal module 190, as shown in FIGS. 1A and 12, which functions to remove gas bubbles that have entered the manifold 140 or other elements of the system 100, and can further function to prevent gas bubbles from entering the manifold 140. Bubbles within the system 100 are disadvantageous because they reduce the effective size of a flow area, which results in increased shear stresses experienced by cells within the system 100. Increased shear stresses can irreversibly damage cells intended for capture and/or analysis, thus preventing further analysis of cells of interest that require viable cells. In a first variation, as shown in FIG. 12, the bubble removal module 190 comprises the reservoir 130, the manifold 140, an outlet reservoir 192 coupled to the manifold outlet 142, and at least one pump 194 coupled to at least one of the reservoir 130 and the outlet reservoir 192. As such, in variations, the manifold outlet 142 can be reversibly coupled to and uncoupled from the outlet reservoir 192 of the bubble removal module 190 and the waste chamber 150, or the waste chamber 150 and the outlet reservoir 192 can be a single element with multi-functionality. In other variations, the manifold 140 can include multiple outlets with or without valved couplers to the outlet reservoir 192 and/or the waste chamber 150, in order to facilitate bubble removal and waste delivery. The pump 194 of the bubble removal module 190 can be configured to apply positive pressure and/or negative pressure, and can be manually driven or computer-driven. In the first variation, the bubble removal module 190 thus allows a fluid (e.g., saline buffer) to be driven in a forward direction from the reservoir 130, through the manifold inlet 141, through a microfluidic device (e.g., a cell capture device 180), out of the manifold outlet 142, and into the outlet reservoir 192, and then driven in a reverse direction from the outlet reservoir 192 to the reservoir 130. Driving the fluid in a forward and a reverse direction is preferably performed by the bubble removal module 190 multiple times, and in an example, is performed up to five times to achieve an adequate level of bubble removal. In the example, the manifold 140 is configured such that fluid flows freely under the action of the pump 194, from the reservoir 130 to the outlet reservoir 192, and from the outlet reservoir 192 to the reservoir 130. Further, the fluid in the example is phosphate buffered saline enriched with bovine serum albumin and ethylenediaminetetraacetic acid (EDTA), and the pump 194 is a syringe pump coupled to the reservoir inlet 131 and configured to provide a positive pressure and a negative pressure. In another variation, the bubble removal module 190 can be any suitable module configured to drive a fluid through the manifold 140 and/or cell capture device 180 in a forward and/or a reverse direction. In yet another variation, the bubble removal module 190 can be any suitable module configured to remove bubbles from the system 100 (e.g., by heat, by agitation, by fluid driving).

As shown in FIG. 1B the system 100 can also further comprise a processor 200, which functions to process data generated upon cell capture and/or analysis, and to detect and control functions performed by elements of the system 100. Preferably, the processor 200 comprises a first module 201 configured to analyze data generated upon cell capture and/or analysis. The processor 200 also preferably comprises a second module 202 configured to detect and enable proper function of elements of the system 100, to facilitate automated capture and/or analysis of cells of interest. The processor 200 is preferably configured to communicate with at least one of a data acquisition module 210, a tag identifying system 220, a heater 170, a temperature control module 171, an actuation system 114, the pump 160, a level sensor 133, 151, and a pressure sensor 161. The processor 200 can, however, additionally or alternatively be configured to communicate with any other suitable element for data processing and system control.

The system 100 can also further comprise a data acquisition module 210 configured to receive and transmit data generated upon cell capture and/or analysis. The data acquisition module 210 is preferably configured to communicate with the processor 200, to govern and receive system 100 parameters related to sample processing and data collection, and to receive data generated in response to cell capture and/or analysis. The data acquisition module 210 can further facilitate signal processing including signal conversion, filtering, conditioning, and amplification. The data acquisition module 210 can be any suitable data acquisition module 210 configured to receive and transmit data generated upon cell capture and/or analysis.

The system 100 can also further comprise a tag identifying system 220 comprising a detection module 221 and at least one tag 222 configured to provide information. The tag identifying system 220 thus functions to read identifying tags of the system 100, in order to receive identifying information and or position information from at least one tag 222. The detection module 221 preferably comprises a charge-coupled device (CCD) camera configured to detect and read a tag comprising a barcode, but can alternatively comprise any other suitable optical device configured to detect and read a tag. In one variation, the detection module 221 comprises an optical sensor configured to detect and read a QR code, and in another variation, the detection module 221 comprises a sensor configured to detect a radio-frequency identification (RFID) chip. The detection module 221 is preferably situated in a position that enables detection of any tag 222 within the system 100. The tag 222 is preferably coupled to at least one of the fluid delivery module 110, the reservoir 130, the manifold 140, the waste chamber 150, the pump 160, the heater 170, and the cell capture device 180, but can alternatively or additionally be coupled to any other suitable element. The tag 222 preferably contains information related to manufacturer information, system element global location, location within an element (e.g., location within a cell capture device), the lot and batch of a fluid, and an expiry date of a fluid. The tag 222 can additionally or alternatively contain any other suitable information.

As a person skilled in the art will recognize from the previous detailed description and from the FIGURES, modifications and changes can be made the described embodiments of the system 100 without departing from the scope of the system 100.

2. Method

Figure 14:
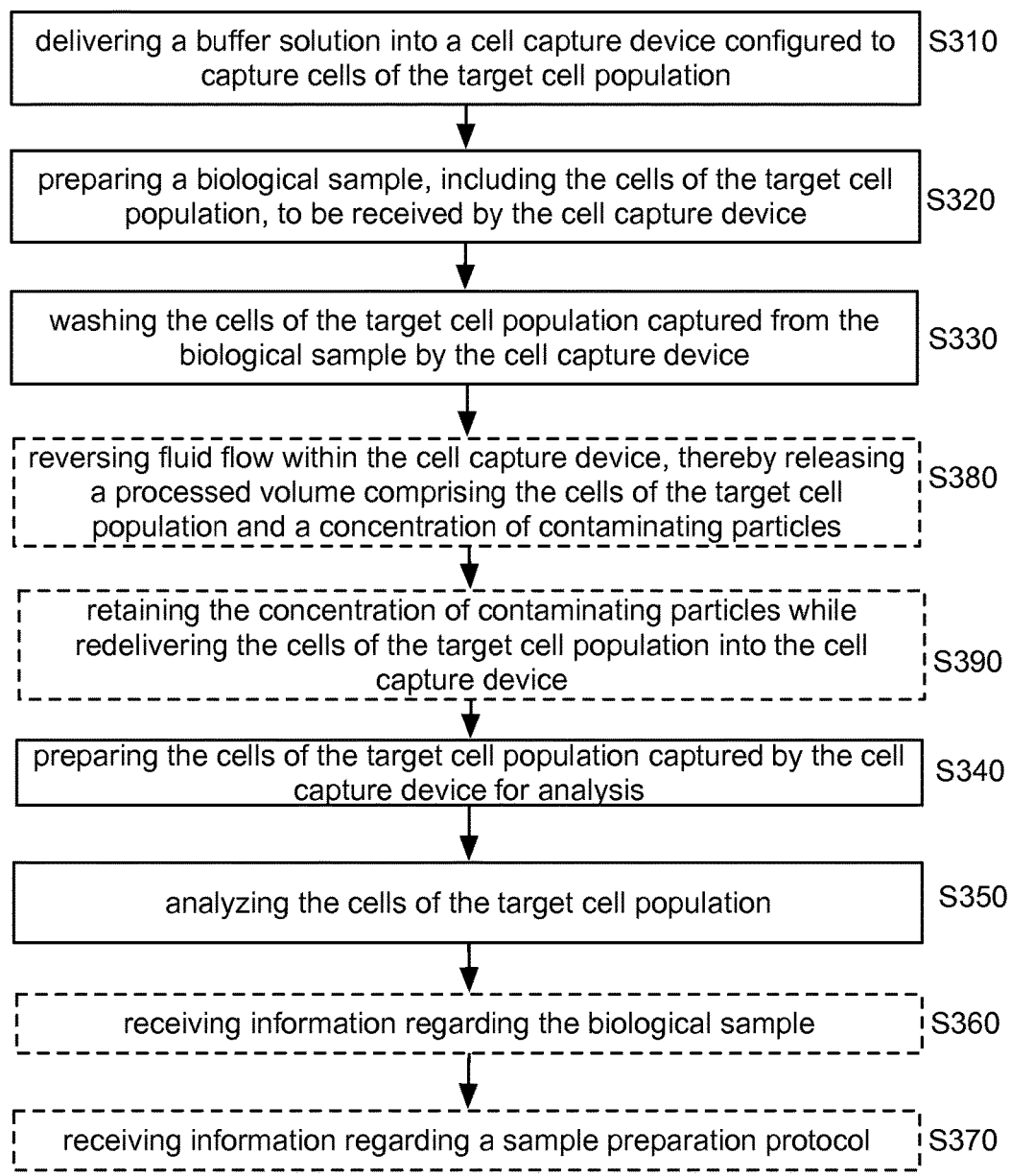
FIG. 14 shows an embodiment of a method for capturing and analyzing cells.

As shown in FIG. 14, an embodiment of a method 300 for capturing and analyzing cells comprises: delivering a buffer solution into a cell capture device configured to capture a target cell population S310, preparing a biological sample, including the target cell population, to be received by the cell capture device S320, washing the target cell population captured from the biological sample by the cell capture device S330, preparing the target cell population captured by the cell capture device for analysis S340, and analyzing the target cell population S350. The method 300 can further comprise receiving information regarding the biological sample S360 and receiving information regarding a sample preparation protocol S370. In embodiments of the method 300 for promoting further purification of captured cells, the method 300 can further comprise reversing fluid flow within the cell capture device, thereby releasing a processed volume comprising the target cell population and a concentration of contaminating particles into a reservoir S380, and retaining the concentration of contaminating particles while redelivering the target cell population into the cell capture device S390. Retention of contaminating particles in S380 may be achieved by binding these contaminating particles to specific contamination-binding surfaces provided by affinity microspheres (magnetic or non-magnetic) introduced at this step into the reservoir S380. The method 300 is preferably implemented by at least a portion of the system 100 described above, but can be implemented by any other suitable system. The method 300 functions to receive, capture, and process at least one biological sample including cells of interest, and can further be used to facilitate analysis of the captured cells of interest. The method 300 can also function to facilitate real-time cell tracking, viable cell retrieval, and selective downstream molecular testing, within a cell capture device, such as a microfluidic chip, or off-chip. Furthermore, the method 300 can provide enhanced purification of captured cells of the target cell population, in order to facilitate processing and analysis without contaminants. The method 300 preferably achieves individual cell capture without antibody coated chambers or biomagnetic tagging, can preferably be used to process unprocessed biological samples (e.g., whole blood) to capture cells of interest, preferably maintains the cell viability throughout capture and retrieval, and preferably facilitates multiplexing biomarkers to identify and analyze captured cells of interest with prepared (e.g., Alexa Fluors, GFP, quantum-dot assays) and user-customizable assays. In a specific embodiment, the method 300 can be used to capture and analyze circulating tumor cells (CTCs), but in other embodiments can be used to capture and analyze any other suitable cell of possible interest.

Step S310 recites: delivering a buffer solution into a cell capture device configured to capture the target cell population, and functions to prepare the cell capture device for receiving a biological sample including the target cell population. Step S310 preferably introduces a priming buffer into the cell capture device to coat a microfluidic pathway of the cell capture device, and to remove bubbles within the cell capture device. In an example, as shown in FIG. 12, delivering a buffer solution into the cell capture device comprises delivering a buffer comprising 1% bovine serum albumin (BSA) and 2 mM ethylenediaminetetraacetic acid (EDTA) in 1× phosphate buffered saline (PBS); however, delivering a buffer solution can comprise delivering any other suitable fluid into the cell capture device. In the example, using a specific example of the system 100 described above, Step S310 can comprise rotating the cylindrical cartridge of the fluid delivery module, such that a chamber containing the buffer solution can be punctured by the actuation system 114. The buffer solution can then flow into the reservoir, to be delivered into the manifold and into the microfluidic chip upon pressure generation by the pump. The buffer solution can then be driven in a forward direction and a reverse direction, by the pump, to adequately remove bubbles from the cell capture device. Step S310 can, however, comprise any other suitable method of delivering a buffer solution into a cell capture device configured to capture the target cell population.

Figure 15:
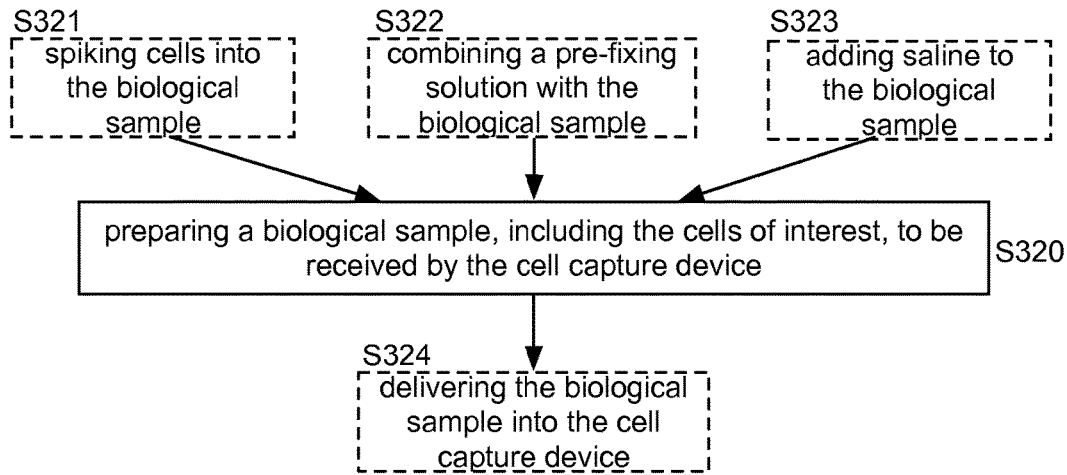
FIG. 15 shows variations of preparing a biological sample.

Step S320 recites: preparing a biological sample, including the target cell population, to be received by the cell capture device, and functions to prepare the biological sample prior to cell capture and/or analysis within the cell capture device. As shown in FIG. 15, Step S320 can comprise one or more of: spiking cells into the biological sample S321, combining a pre-fixing solution with the biological sample S322, adding saline to the biological sample S323, and delivering the biological sample into the cell capture device S324; however, Step S320 can additionally or alternatively comprise any other suitable biological sample preparation step. For instance, the biological sample can include a cell population of interest as the target cell population, thus eliminating a need for spiking cells into the biological sample. In an example, using a specific example of the system 100 described above, Step S320 can comprise delivering the biological sample (e.g., 2 mL of whole blood), with a cell population of interest (e.g., MCF7 breast cancer cells, SKBR3 breast cancer cells, LnCAP prostate cancer cells, PC3 prostate cancer cells, HT29 colorectal cancer cells) prepared with or without cell spiking, to the reservoir and rotating the cylindrical cartridge of the fluid delivery module, such that a chamber containing an appropriate biological sample preparation solution can be punctured by the actuation system 114. The biological sample preparation solution can then flow into the reservoir, to be combined with the biological sample, and then be delivered into the microfluidic chip upon pressure generation by the pump. Step S320 can, however, comprise any other suitable method of preparing a biological sample, including the target cell population, to be received by the cell capture device.

Step S330 recites: washing the target cell population captured from the biological sample by the cell capture device, and functions to remove waste within the cell capture device, such that captured cells of the target cell population are substantially separated from waste and/or contaminating particles within the cell capture device. In an example, washing the target cell population captured from the biological sample comprises delivering a wash solution comprising 0.1% Tween in 1×PBS; however, delivering a wash solution can comprise delivering any other suitable fluid into the cell capture device to wash the cells of interest. In the example, using a specific example of the system 100 described above, Step S330 can comprise rotating the cylindrical cartridge of the fluid delivery module, such that a chamber containing the wash solution can be punctured by the actuation system 114. The wash solution can then flow into the reservoir, to be delivered into the manifold and into the microfluidic chip upon pressure generation by the pump. Step S330 can, however, comprise any other suitable method of washing the target cell population captured from the biological sample by the cell capture device.

Figure 16:
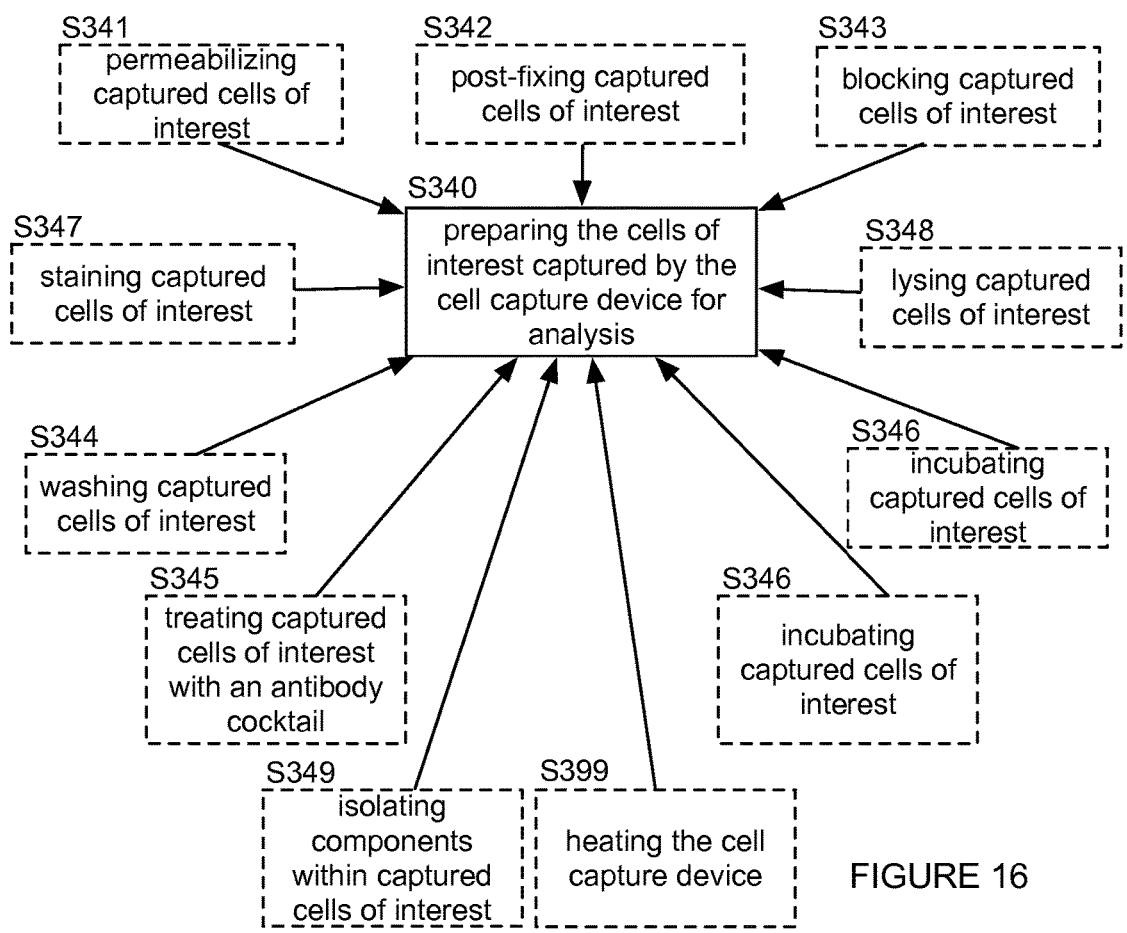
FIG. 16 shows variations of preparing cells of interest, captured by a cell capture device, for analysis.

Step S340 recites: preparing the target cell population captured by the cell capture device for analysis, and functions to process the target cell population according to a given protocol to facilitate analysis. As shown in FIG. 16, Step S340 can comprise delivering a processing reagent to the target cell population, and in variations, can include one or more of: permeabilizing captured cells of the target cell population S341, post-fixing captured cells of the target cell population S342, blocking captured cells of the target cell population S343, washing captured cells of the target cell population S344, treating captured cells of the target cell population with an antibody cocktail S345, incubating captured cells of the target cell population S346, staining captured cells of the target cell population S347, lysing captured cells of the target cell population S348, isolating components within captured cells of the target cell population S349, and heating the cell capture device S399. Step S340 can additionally or alternatively comprise any suitable step that prepares the cells of interest captured by the cell capture device for analysis, such as delivering a hybridization buffer to the cells of interest, delivering control probes to the cells of interest, dehydrating the cells of interest, and/or denaturing the cells of interest. In one variation, Step S340 can prepare cells of the target cell population for an analysis requiring a stain (e.g. fluorescent stain or histological stain). In another variation, Step S340 can prepare cells of the target cell population for an analysis involving electrophoresis. In yet another variation, Step S340 can prepare cells of the target cell population for a molecular diagnostic assay, such as PCR. Step S340 can comprise rotating the cylindrical cartridge of the fluid delivery module, such that a chamber containing a desired reagent solution can be punctured by the actuation system 114. In an example of Step S340, using a specific example of the system 100 described above, Step S340 can comprise rotating the cylindrical cartridge of the fluid delivery module, such that a chamber containing an appropriate fluid can be punctured by the actuation system 114. The fluid can then flow into the reservoir, to be delivered into the manifold and into the microfluidic chip upon pressure generation by the pump. The example of Step S340 can further comprise activating a heater to heat the microfluidic chip, and can further comprise thermocycling or incubating the microfluidic chip by controlling the heater with the processor. Step S340 can, however, comprise any other suitable method of preparing cells of the target cell population captured by the cell capture device for analysis.

Step S350 recites: analyzing the target cell population, and functions to generate a set of data to characterize features of captured cells of the target cell population. The target cell population t can be analyzed within the cell capture device, or can be analyzed outside of the cell capture device. In a first variation, Step S350 can comprise delivering the cell capture device, containing captured cells of the target cell population to a separate module (e.g., a microscope, an imaging system) after preparing captured cells of interest for an analysis requiring a stain. In a second variation, Step S350 can comprise delivering captured cells of the target cell population from the cell capture device, and/or delivering cellular components from cells of the target cell population captured using the cell capture device and a removal tool, such that cells of the target cell population and/or cellular components can be analyzed. In a third variation, Step S350 can comprise delivering cells of the target cell population to be cultured for further analysis. In a fourth variation, Step S350 can comprise delivering cellular components into an electrophoresis module for electrophoretic separation. In yet another variation Step S350 can comprise detecting nucleic acids within the cell capture device after preparing the biological sample for PCR. Step S350 can, however, comprise any other suitable method of analyzing the target cell population.

The method 300 can further comprise Step S360, which recites receiving information regarding the biological sample. Step S360 functions to facilitate identification and processing of a specific biological sample. Step S360 is preferably performed before Step S310, such that an automated system can be prepared to process and analyze a biological sample based on the information. Step S360 can alternatively be performed before or after any suitable step of the method 300. Step S360 can allow a user to input information about the biological sample, or can automatically receive information about the biological sample using a tag identifying system. Step S360 can, however, include any other suitable method of receiving information regarding the biological sample.

The method can further comprise Step S370, which recites receiving information regarding a sample preparation protocol. Step S370 functions to facilitate processing of a biological sample according to a specific sample preparation protocol. Step S370 is preferably performed before Step S310, such that an automated system can be prepared to process and analyze a biological sample based upon the information. For example, Step S370 can enable automatic alignment of chambers of a set of chambers of a fluid delivery module, with a reservoir configured to deliver processing reagents into a cell capture device. In a specific example, a sequence of alignment commands can be generated that control rotation of a cylindrical cartridge containing isolated processing reagents, thereby automating processing of the biological sample according to the sample preparation protocol. Step S370 can alternatively be performed before or after any suitable step of the method 300. Step S370 can allow a user to input information about the sample preparation protocol, or can automatically receive information about the sample preparation protocol using a tag identifying system. Step S370 can, however, include any other suitable method of receiving information regarding the sample preparation protocol.

In embodiments of the method 300 for promoting further purification of captured cells of the target cell population, the method 300 can further comprise Step S380, which recites reversing fluid flow within the cell capture device, thereby releasing a processed volume comprising the target cell population and a concentration of contaminating particles into a reservoir. Step S380 functions to drive a volume comprising captured cells of the target cell population and a concentration of contaminating particles toward a reservoir, wherein the target cell population can be separated from the concentration of contaminating particles. In some variations of Block S380, however, the entire target cell population may not be driven into the reservoir by reversing flow, but rather, only a portion of the contents of the cell capture device may be transmitted back to the reservoir by reversing flow. In one variation, Step S380 can further comprise selectively tagging the contaminating particles with a marker S384 (e.g., incubating contaminating particles with a particle-specific marker) configured to bind to microparticles that facilitates separation. Step S380 can also further comprise binding the tagged contaminating particles to microparticles S386. In an example of Step S384, the contaminating cells are white blood cells, which are tagged with biotinylated CD45 by delivering the biotinylated CD45 in a forward direction into the cell capture device with captured cells of the target cell population and white blood cells and incubating the white blood cells with the biotinylated CD45 antibodies. In an example of Step S386, the microparticles comprise streptavidin-coated magnetic beads, which are bound to the CD45-tagged white blood cells by driving a solution of the streptavidin-coated magnetic beads, in a reverse direction, into the cell capture device and incubating the CD45-tagged white blood cells with the streptavidin-coated magnetic beads. Then, in an example of Step S380, the white blood cells bound to magnetic beads and the cells of the target cell population are driven in a reverse direction toward a reservoir that enables isolation of the captured cells of interest. In other variations, Steps S380, S384, and/or S386 can alternatively comprise marking the captured cells of interest and/or binding the captured cells of interest to microparticles that facilitate separation of the captured cells of interest from contaminating particles. In still other variations, Steps S380, S384, and/or S386 can comprise using any other suitable combination of markers and binding particles that facilitate separation of contaminating particles from the cells of interest.

Also shown in FIG. 14, the method can further comprise Step S390, which recites retaining the concentration of contaminating particles while redelivering the cells of the target cell population into the cell capture device. Step S390 functions to isolate the contaminating particles while allowing manipulation of the captured cells of the target cell population for further processing and analysis. Preferably, the contaminating particles are retained within the reservoir by a magnet proximal to the reservoir; however, the contaminating particles can alternatively be retained within any other suitable element of a system for capturing cells, including a manifold, a cell capture device, and/or an outlet reservoir. In one variation, using an embodiment of the system 100 above comprising a magnet 165, a magnetic field provided by the magnet can retain the concentration of contaminating particles, which are bound to magnetic beads, within a reservoir while the cells of the target cell population are re-driven in a forward direction into the cell capture device. In alternative variations, the concentration of contaminating particles can be retained in any suitable manner (e.g., by finer degrees of size-based separation, hydrodynamic focusing, focusing based upon density or fluid behavior). Furthermore, the captured cells of interest can additionally or alternatively be isolated and transferred to another module for further processing and analysis.

In specific examples, Steps S380 and S390 can reduce the number of contaminating white blood cells within a whole blood sample by a 4-log reduction. In the specific examples, the method 300 without Steps S380 and S390 can provide a 2-3 log reduction in the number of contaminating white blood cells within a whole blood sample. Collectively, the method 300 including Steps S380 and S390 can thus substantially purify a volume of captured cells the target cell population of any non-target particles that are of similar size to the captured target cells. The method 300 can, however, comprise any additional suitable step(s) that enable(s) removal of non-target particles from a biological sample. Specific examples of the method and system are presented in Sections 2.1-2.4 below.

2.1 First Specific Example of the Method and System

Figure 17:
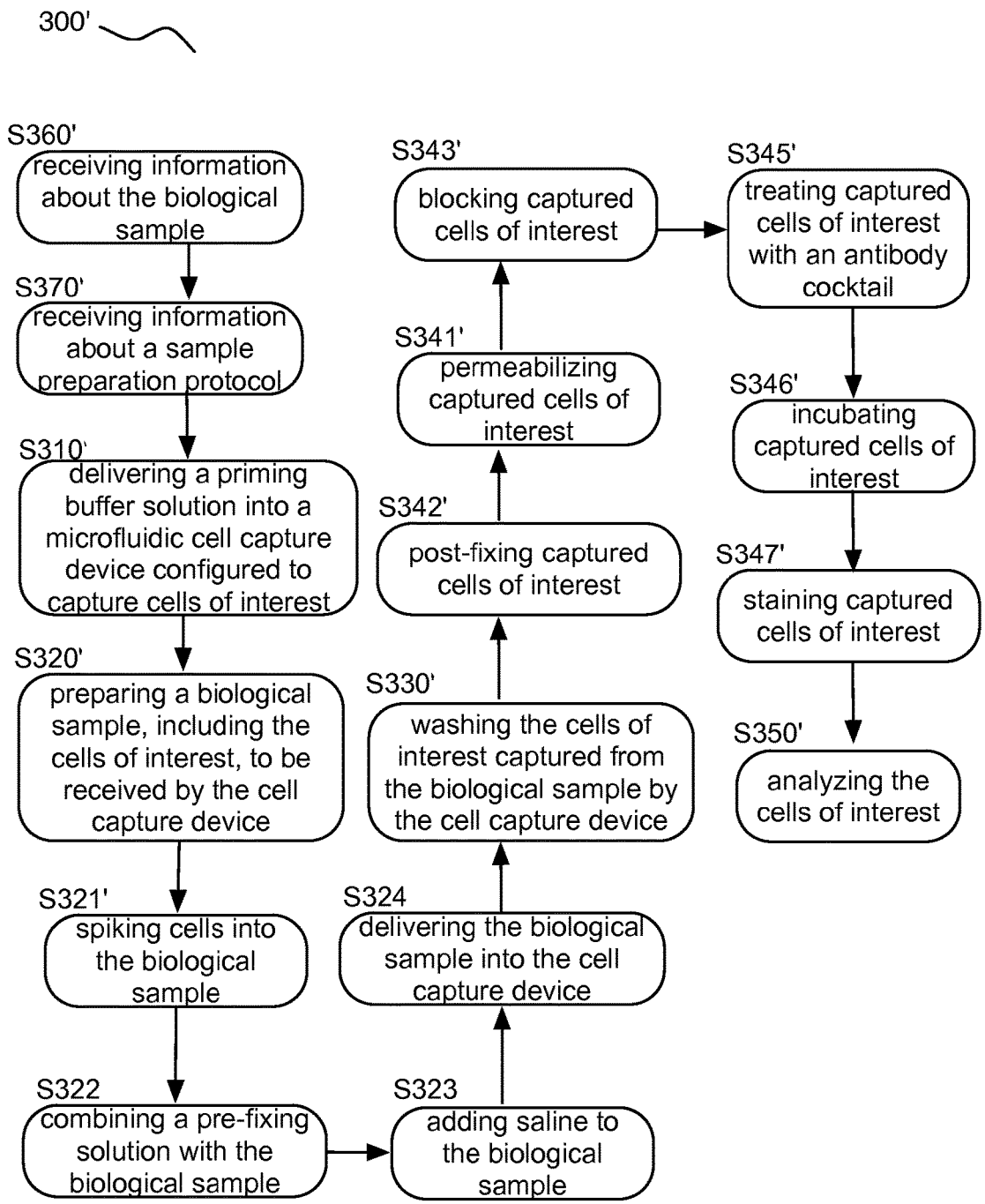
FIG. 17 shows a flowchart of a first specific example of a method for capturing and analyzing cells.

As shown in FIG. 17, a first specific example of the method 300' for capturing, fluorescently staining, and analyzing cells of a target cell population comprises: receiving information regarding the biological sample S360'; receiving information regarding a sample preparation protocol S370'; delivering a priming buffer solution into a cell capture device configured to capture cells of the target cell population S310'; preparing a biological sample, including the target cell population, to be received by the cell capture device S320'; spiking cells into the biological sample S321'; combining a pre-fixing solution with the biological sample S322'; adding saline to the biological sample S323'; and delivering the biological sample into the cell capture device S324'. The specific example of the method 300' further comprises washing the cells of the target cell population captured from the biological sample S330'; post-fixing captured cells of the target cell population S342'; permeabilizing captured cells of the target cell population S341'; blocking captured cells of the target cell population S343'; treating captured cells of the target cell population with an antibody cocktail S345'; incubating captured cells of the target cell population S346'; staining captured cells of the target cell population S347'; and analyzing the cells of the target cell population S350'. In the specific example, washing the cells of the target cell population captured from the biological sample S330' also occurs after each of Steps S342', S341', S343', S345', and S347'.

In the first specific example of the method 300', the priming buffer solution comprises 1% BSA and 2 mM EDTA in 1×PBS; the pre-fixing solution comprises 0.8% paraformaldehyde (PFA) in 1×PBS; washing the cells of interest comprises using a wash buffer of 0.1% Tween in 1×PBS; post-fixing captured cells of interest comprises using a post-fixing solution of 4% PFA in 1×PBS; permeabilizing captured cells of interest comprises using a permeabilization buffer of 0.1% Triton in 1×PBS; blocking captured cells of interest comprises using a Mocking solution of 5% goat serum in 1×PBS; the antibody cocktail comprises a first cocktail of 1:200 PanCK (10 µL), 1:200 Zym 5.2 (10 µL), and 1:200 CD45 (5 µL) in 975 µL of 1×PBS, and a second cocktail of Alexa 488 IgG1 4 µg/mL at a 1:500 dilution and Alexa 594 IgG2a 3 µg/mL at a 1:700 dilution; and staining captured cells of interest comprises a Hoescht stain at a concentration of 1 µg/mL. The first specific example thus facilitates capture of individual target cells of the target cell population, processes the target cell population, and enables analysis of the cells of the target cell population by way of a fluorescence detection assay.

Figure 18:
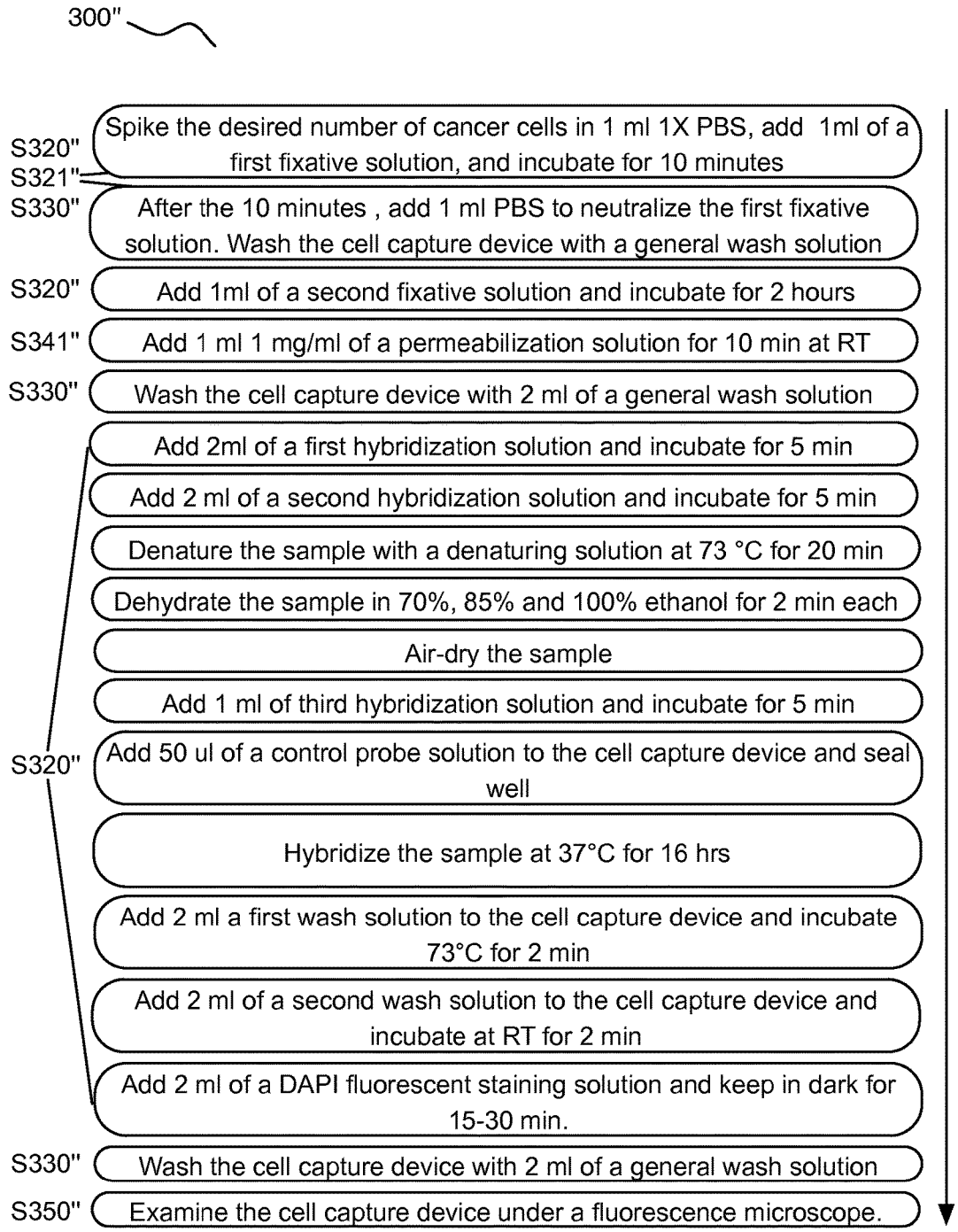
FIG. 18 shows a flowchart of a second specific example of a method for capturing and analyzing cells.

2.2 Second Specific Example of the Method and System—Fluorescence In Situ Hybridization (FISH) Assay As shown in FIG. 18, a second specific example of the method 300" for capturing, fluorescently staining, and analyzing cells of interest comprises: receiving information regarding the biological sample S360"; receiving information regarding a sample preparation protocol S370"; delivering a priming buffer solution into a cell capture device configured to capture cells of the target cell population S310"; preparing a biological sample, including the cells of the target cell population, to be received by the cell capture device S320"; spiking cells into the biological sample S321"; combining a pre-fixing solution with the biological sample S322"; adding saline to the biological sample S323"; and delivering the biological sample into the cell capture device S324". The specific example of the method 300" further comprises washing the cells of the target cell population captured from the biological sample S330"; preparing the cells of the target cell population captured by the cell capture device for analysis S340"; incubating captured cells of the target cell population S346"; staining captured cells of the target cell population S347"; and analyzing the cells of the target cell population S350".

In the second specific example, as shown in FIG. 18, Step S320" comprises combining the biological sample with a first fixative solution, incubating the biological sample with the first fixative solution for 10 minutes, and neutralizing the first fixative solution. Step S320" further comprises combining the biological sample with a second fixative solution, incubating the biological sample with the second fixative solution for 2 hours, combining the biological sample and the second fixative solution with a permeabilization solution for 10 minutes at room temperature. Step S340" comprises combining the biological sample with a first hybridization solution and a second hybridization solution and incubating the biological sample with the hybridization solutions for 5 minutes at room temperature (in two stages), combining the biological sample and the hybridization solution with a denaturing solution and incubating the solution at 73 C for 20 minutes, dehydrating the biological sample, and air-drying the biological sample. Step S340" further comprises combining the biological sample with a third hybridization solution and incubating the biological sample with the third hybridization solution for 5 minutes at room temperature, combining the biological sample and the third hybridization solution with a control probe solution, incubating the biological sample-hybridization-control probe solution for 16 hours at 37 C, and washing the biological sample with a first wash solution and a second wash solution. Similar to the first specific example, the second specific example of the method 300" comprises washing the cells of interest captured from the biological sample S330" after each of neutralizing the fixative solution, combining the biological sample and the second fixative solution with a digestive solution, and staining captured cells of interest from the biological sample, using a general wash solution.

In the second specific example of the method 300", the first fixative solution comprises 1 mL of 0.8% paraformaldehyde (PFA); the second fixative solution comprises 1 mL of 4% paraformaldehyde; the permeabilization solution comprises 1 mg/mL pepsin; the first hybridization solution comprises 2× saline sodium citrate buffer (SSC); the second hybridization solution comprises 2×SSC buffer and 50% formamide; the denaturing solution comprises 70% formamide and 2×SSC buffer (pH 7.0-8.0); the third hybridization solution comprises 5M NaCl, 1M Tris-HCl (pH7.5), 50% formamide, 0.4 mg/mL salmon sperm DNA, and 10% SDS; the control probe solution comprises 50% formamide, 2×SSC buffer, 10% dextran sulfate, 0.4 mg/mL salmon sperm DNA, and 20 ng/uL of control probe; the first wash solution comprises 0.4×SSC buffer and 0.3% NP-40 in deionized water; the second wash solution comprises 2×SSC buffer and 0.1% NP-40 in deionized water; and the general wash solution comprises 1×PBS. Dehydrating the biological sample comprises subjecting the biological sample to an ethanol gradient of 70%, 85%, and 100% ethanol. The second specific example thus facilitates capture of individual target cells of interest, processes the target cells of interest, and enables analysis of the target cells of interest by way of a fluorescence in situ hybridization assay.

2.3 Third Specific Example of the Method and System—Single Cell In Situ Polymerase Chain Reaction (PCR)

Figure 19:
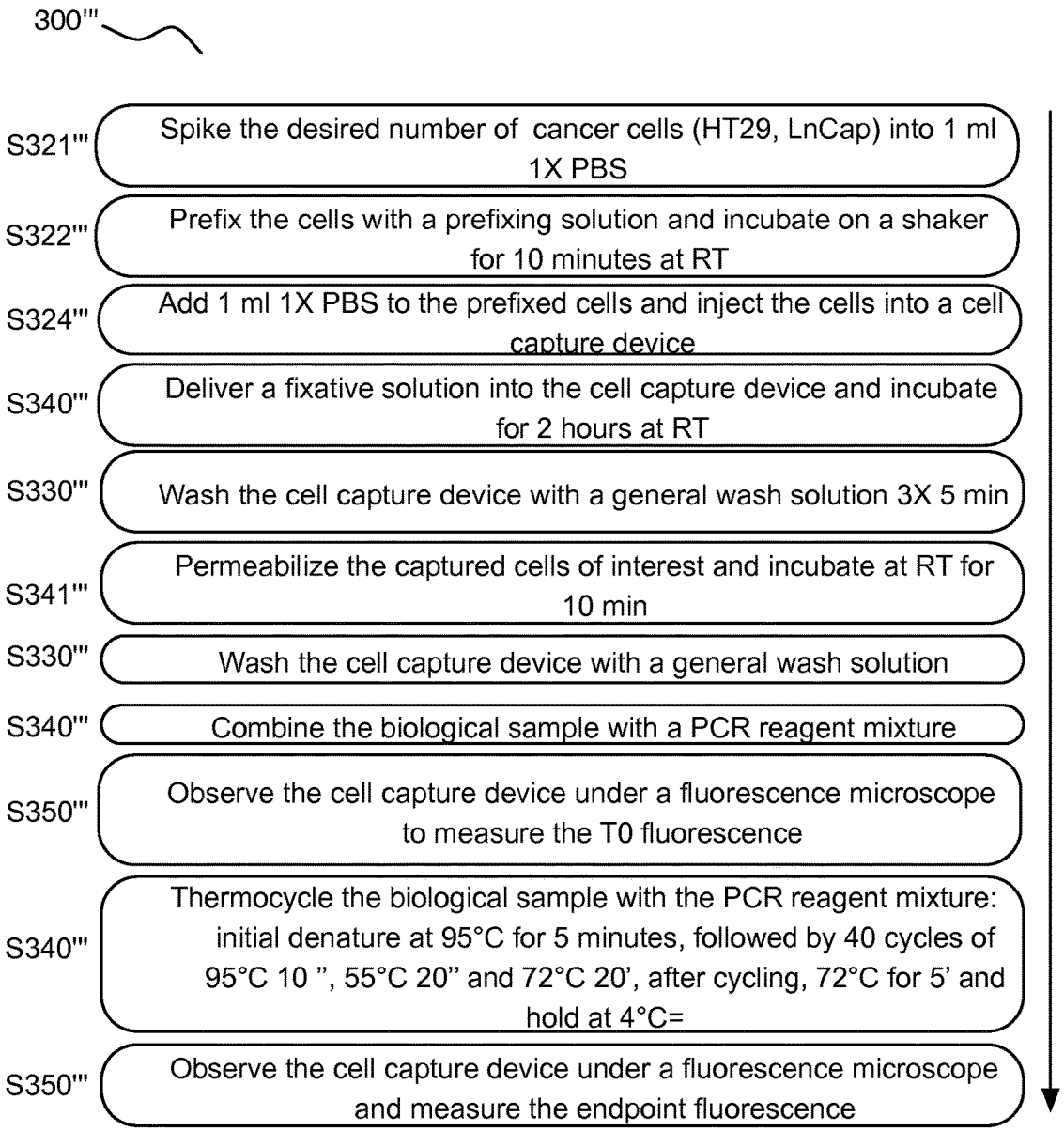
FIG. 19 shows a flowchart of a third specific example of a method for capturing and analyzing cells.

As shown in FIG. 19, a third specific example of the method 300''' for capturing, fluorescently staining, and analyzing cells of a target cell population comprises: receiving information regarding the biological sample S360'''; receiving information regarding a sample preparation protocol S370'''; delivering a priming buffer solution into a cell capture device configured to capture cells of interest S310'''; preparing a biological sample, including the cells of the target cell population, to be received by the cell capture device S320'''; spiking cells (HT29 cancer cells) into the biological sample S321'''; combining a pre-fixing solution with the biological sample S322'''; adding saline to the biological sample S323'''; and delivering the biological sample into the cell capture device S324''. The specific example of the method 300''' further comprises washing the cells of the target cell population captured from the biological sample S330'''; preparing the cells of the target cell population captured by the cell capture device for analysis S340'''; permeabilizing captured cells of the target cell population with a permeabilization solution S341'''; incubating captured cells of the target cell population S346'''; staining captured cells of the target cell population S347'''; and analyzing the cells of the target cell population S350'''.

In the third specific example, as shown in FIG. 19, Step S320''' comprises combining the biological sample with a fixative solution, incubating the biological sample with the fixative solution for 2 hours at room temperature, and neutralizing the fixative solution. Step S340'' comprises combining the biological sample with a PCR reagent mixture and thermocycling the biological sample combined with the PCR reagent mixture. Similar to the first and second specific examples, the third specific example of the method 300''' comprises washing the cells of the target cell population captured from the biological sample S330''' after each of incubating the biological sample with the fixative solution and permeabilizing captured cells of the target cell population, with a general wash solution.

In the third specific example of the method 300'', the prefixing solution comprises 1 mL of 0.8% paraformaldehyde (PFA); the fixative solution comprises 1 mL of 4% paraformaldehyde; the permeabilization solution comprises 1 mg/mL pepsin; the PCR reagent mixture comprises 1× (Mg2+ free) PCR buffer, 200 uM of each dNTPs, 300 nM of a gene specific forward primer, 300 nM of a gene specific reverse primer, 300 nM of Ampliflour UniPrimer II, 4.0 mM of MgCl2, 2.5 units of TAQ DNA polymerase, and deionized water. Thermocycling comprises establishing an initial denature at 95 C for 5 minutes, followed by 40 cycles of the following parameters: 95 C for 10 seconds, 55 C for 20 seconds, and 72 C for 20 minutes. After cycling, the biological sample is held at 72 C for 5 minutes and then maintained at 4 C. The third specific example thus facilitates capture of individual target cells of interest, processes the target cells of interest, and enables analysis of the target cells of interest by way of a single cell in situ PCR assay.

Exemplary results of the third specific example of the method 300''' involved single cell PCR analysis using an exemplary cell capture device and MCF7 cells spiked in buffer. In the third specific example, BrightField imaging enabled visualization of MCF7 cells within the cell capture device, fluorescence imaging with a FITC filter, showed no fluorescent signal prior to amplification by single cell PCR, and fluorescence imaging with a FITC filter showed marked increases in fluorescent signal post amplification by single cell PCR.

Figure 20:
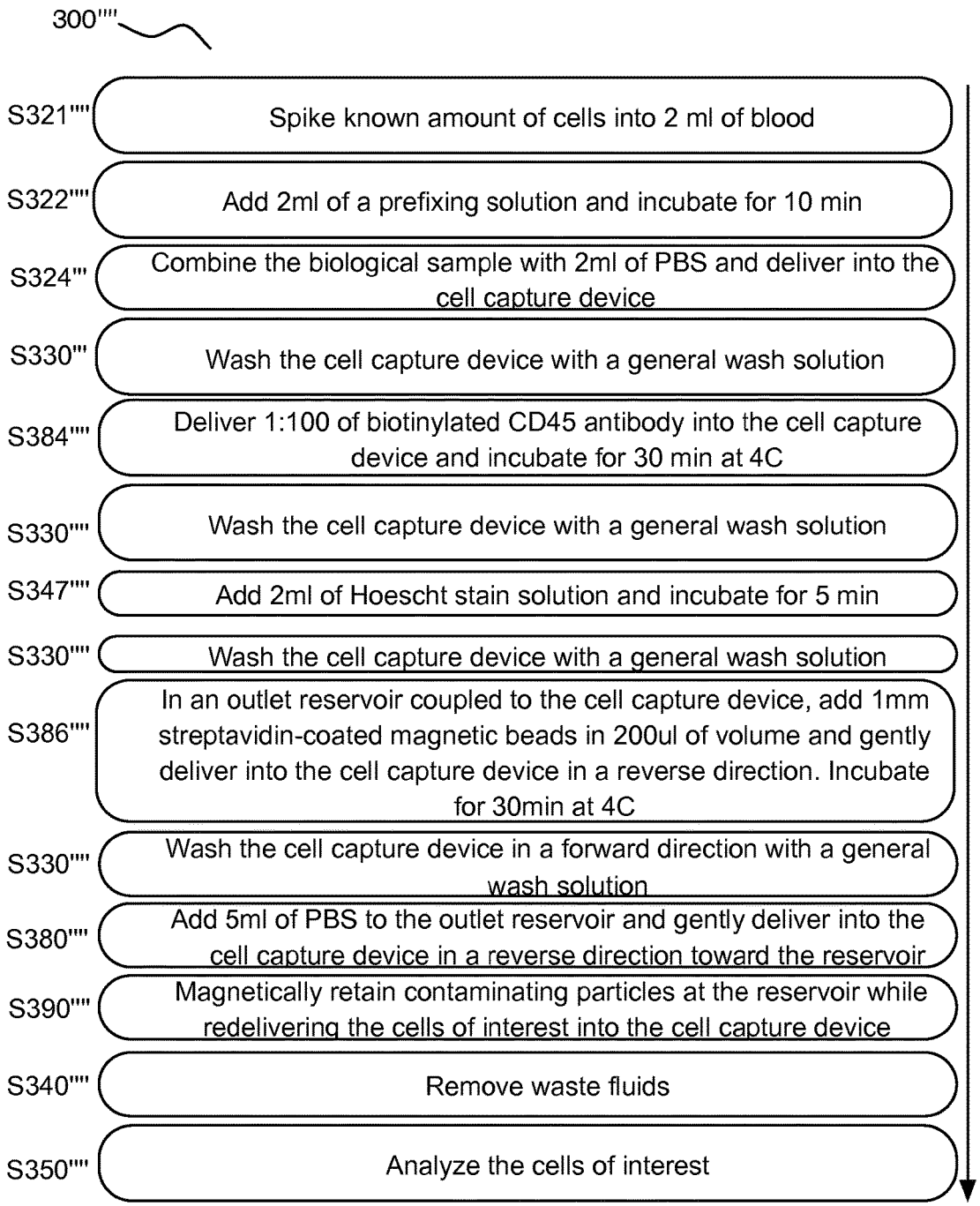
FIG. 20 shows a flowchart of a fourth specific example of a method for capturing and analyzing cells.

2.4 Fourth Specific Example of the Method and System—Magnetic Purification of Captured Target Cells As shown in FIG. 20, a fourth specific example of the method 300'''' for capturing, fluorescently staining, and analyzing cells of a target cell population comprises delivering a priming buffer solution into a cell capture device configured to capture cells of the target cell population S310''''; preparing a biological sample, including the cells of the target cell population, to be received by the cell capture device S320''''; spiking cells into the biological sample S321''''; combining a pre-fixing solution with the biological sample S322''''; adding saline to the biological sample S323''''; and delivering the biological sample into the cell capture device S324''''. The specific example of the method 300'' further comprises washing the cells of the target cell population captured from the biological sample S330''''; binding contaminating particles (i.e., white blood cells) of the biological sample with biotinylated CD45 S384'''' by running the biotinylated CD45 in a forward direction into the cell capture device; binding the CD45-tagged contaminating particles to streptavidin-coated magnetic beads S386'''' by running a solution comprising the streptavidin-coated magnetic beads in a reverse direction into the cell capture device; reversing fluid flow within the cell capture device, thereby releasing a processed volume comprising the cells of the target cell population and the CD45-bound contaminating particles coupled with magnetic beads into a reservoir S380''''; magnetically retaining the CD45-bound contaminating particles coupled with magnetic beads within the reservoir while redelivering the cells of the target cell population into the cell capture device S390''''; and staining the cells of interest with a staining solution S347''''. Similar to other specific examples, washing S330'''' in the fourth specific example after each of Steps S324'''', S384'''', S347'''', and S386''''.

In the fourth specific example of the method 300'''', the prefixing solution comprises 2 mL of 0.8% paraformaldehyde (PFA) provided for an incubation time of 10 minutes; the biotinylated CD45 is provided at a ratio of moo; the staining solution comprises 2 mL of a Hoescht stain and is provided for 5 minutes; and the solution comprising the streptavidin-coated magnetic beads is provided in a 200 uL fluid volume. The fourth specific example thus facilitates capture of individual target cells of interest, processes the target cells of interest, and further separates contaminating cells from captured target cells of interest by way of a magnetic separation protocol.

The system 100 and/or method 300 of the preferred embodiment and variations thereof can be embodied and/or implemented at least in part as a machine configured to receive a computer-readable medium storing computer-readable instructions. The instructions are preferably executed by computer-executable components preferably integrated with the system 300 and one or more portions of the processor 350. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of methods according to preferred embodiments, example configurations, and variations thereof. In this regard, each block in the flowchart or block diagrams can represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for capturing and analyzing a target cell population from a biological sample, comprising:
   at a fluid delivery module of a sample processing system, rotating a first chamber, of a cylindrical cartridge having a set of chambers, into alignment with a reservoir configured to receive a buffer solution from the first chamber;
   delivering the buffer solution from the first chamber into the reservoir upon puncturing an inferior portion of the first chamber, and from the reservoir into a cell capture device configured to capture the target cell population;
   delivering the biological sample, including the target cell population, into the cell capture device, thereby capturing the target cell population, in single-cell format, at the cell capture device; and
   washing the target cell population captured from the biological sample at the cell capture device, by way of the fluid delivery module; and
   delivering the cell-capture device from the sample processing system, thereby preparing the target cell population captured at the cell capture device for analysis.

2. The method of claim 1, further comprising driving flow of the buffer solution in a forward direction and in a reverse direction through the cell capture device, thereby removing bubbles trapped in the cell capture device.

3. The method of claim 1, further comprising reversing fluid flow within the cell capture device after delivering the biological sample into the cell capture device, thereby releasing a processed volume comprising the target cell population and a concentration of contaminating particles back into the reservoir.

4. The method of claim 3, further comprising selectively binding particles of the concentration of contaminating particles to magnetic beads, and retaining the concentration of contaminating particles at the reservoir by way of a magnet proximal the reservoir, while redelivering the target cell population into the cell capture device in the forward direction.

5. The method of claim 4, wherein binding particles of the concentration of contaminating particles to magnetic beads comprises binding a concentration of white blood cells to streptavidin-treated magnetic beads within the reservoir, and wherein redelivering the target cell population into the cell capture device comprises redelivering a CTC population into the cell capture device.

6. The method of claim 3, further including tagging the concentration of contaminating particles with a marker configured to facilitate separation of the concentration of contaminating particles from the target cell population, at the reservoir.

7. The method of claim 1, further including rotating a second chamber of the cylindrical cartridge of the fluid delivery module into alignment with the reservoir, and wherein preparing the target cell population captured at the cell capture device for analysis includes puncturing a second seal enclosing the second chamber to facilitate flow of a processing reagent into the reservoir and into the cell capture device, with the target cell population.

8. The method of claim 1, further including positioning the cell capture device between a manifold, configured to facilitate fluid flow throughout the cell capture device, and a heater, and heating the target cell population at the cell capture device by way of the heater.

9. The method of claim 8, further including delivering a coolant into a fluid network of a plate coupled to the heater, thereby cooling the target cell population at the cell capture device.

10. The method of claim 1, further including receiving information regarding a sample preparation protocol for the biological sample, wherein preparing the target cell population for analysis comprises automatically rotating chambers of the set of chambers of the fluid delivery module into alignment with the reservoir, based upon the sample preparation protocol.

* * * * *